United States Patent
Okano et al.

(10) Patent No.: US 6,391,296 B1
(45) Date of Patent: May 21, 2002

(54) METHOD OF STABILIZING USEFUL PROTEIN AND USEFUL PROTEIN COMPOSITIONS

(75) Inventors: Fumiyoshi Okano; Katsushige Yamada, both of Aichi; Masatoshi Watanabe, Gifu; Naomi Hara, Shizuoka; Akira Yanai, Shiga, all of (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/269,833

(22) PCT Filed: Jul. 31, 1998

(86) PCT No.: PCT/JP98/03431

§ 371 Date: Apr. 26, 1999

§ 102(e) Date: Apr. 26, 1999

(87) PCT Pub. No.: WO99/06429

PCT Pub. Date: Feb. 11, 1999

(30) Foreign Application Priority Data

Aug. 1, 1997 (JP) ............................... 9-208085
Aug. 1, 1997 (JP) ............................... 9-208086
Dec. 25, 1997 (JP) ............................... 9-357872

(51) Int. Cl.$^7$ .................. A61K 45/00; A61K 38/21; C12C 11/00; C12G 1/00; C12P 21/04

(52) U.S. Cl. .................. 424/85.1; 424/85.5; 426/11; 426/12; 426/15; 426/16; 426/28; 426/600; 435/69.51

(58) Field of Search ........................... 424/85.5; 426/16, 426/11, 12, 15, 28, 29, 592, 600; 435/69.51

(56) References Cited

U.S. PATENT DOCUMENTS 5,955,069 A * 9/1999 Uchino et al. ............. 424/85.5
5,993,865 A * 11/1999 Bech et al. .................. 426/16

FOREIGN PATENT DOCUMENTS

| JP | 6-321803 | 11/1994 |
| WO | WO 97/41885 | 11/1997 |
| WO | WO 98/51328 | 11/1998 |

* cited by examiner

*Primary Examiner*—Jeffrey Fredman
*Assistant Examiner*—Arun Chakrabarti
(74) *Attorney, Agent, or Firm*—Schnader Harrison Segal & Lewis LLP

(57) ABSTRACT

A method of stabilizing a useful protein by mixing a useful protein and an aqueous solution of a compound having the basic structure of arabic acid, and a stabilizied useful protein compositon containing a useful protein and a compound having the basic structure of arabic acid; gum arabic is preferred as a compound having the basic structure of arabic acid, and examples of a useful protein include cytokine and interferon; and a production method for canine interferon-γ and stabilization thereof.

9 Claims, 1 Drawing Sheet

METHOD OF STABILIZING USEFUL PROTEIN AND USEFUL PROTEIN COMPOSITIONS

TECHNICAL FIELD

The present invention relates to a method of stabilizing and preserving a useful protein, and a composition capable of stably holding the biological activity of a useful protein. Particularly the present invention relates to a method of stabilizing and preserving a useful protein, particularly, interferon of a mammal such as a dog or cat, and a composition capable of stably holding the activity thereof.

BACKGROUND ART

Proteins, particularly enzymes, useful proteins having biological activity, and the like can be mass-produced at low cost by gene recombination technology, and are thus used in various fields, particularly medicines, diagnostics, and foods. On the other hand, proteins are inactivated when the primary structure thereof is damaged due to degradation, and the function thereof greatly depends upon the higher-order structure. Therefore, proteins also have a problem in that the higher-order structure is easily, damaged due to various outside factors (temperature, changes over time, light, and pH) depending upon the types of proteins, thereby losing their function (biological activity). Thus, research is performed on a method of stabilizing the higher-order structure of a protein, and maintaining the biological activity thereof.

At present, a useful general method of stabilizing a protein comprises mixing it with another protein (gelatin, albumin, serum, collagen, or the like). Mixing with gelatin or serum permits preservation for a relatively long period of time, and there are many known drug products of enzymes and biologically active proteins produced by such a mixing method (Japanese Unexamined Patent Publication Nos. 2-264728, 2-49734, 54-80406, and 56-68607).

Stabilization of interferon (IFN) which is a biologically active substance having an immunomodulation action, and an antiviral action and which attracts attention in medical applications has been described. Japanese Unexamined Patent Publication Nos. 60-228422, 60-34919, 61-137828 and 60-260523 disclose a stabilization method comprising mixing with albumin or gelatin. Examples of known compounds having the protein stabilizing action other than proteins include saccharides, particularly monosaccharides, disaccharides, and polysaccharides such as dextran and hydroxyethyl starch (Japanese Unexamined Patent Publication Nos. 59-181223, 61-44826 and 60-155136 and Japanese Examined Patent Publication No. 6-51641), cyclodextrin, and polyhydric sugar alcohols (Japanese Unexamined Patent Publication No. 58-92691, and Japanese Examined Patent Publication No. 3-500882). There is also a method of making dominant a dimer of IFN-$\gamma$ having high activity using lactobionic acid (Japanese Examined Patent Publication No. 3-501604).

There are many reports of mixtures of gum arabic and proteins in which an aqueous gum arabic solution is used as a dispersing agent for a medicine (Japanese Unexamined Patent Publication No. 6-321803). However, there are also special report examples including: an example in which in production of an antibody, the amount of the antibody produced is increased by administering a mixture of a protein as an antigen and gum arabic than by administering a protein alone (Japanese Examined Patent Publication No. 58-23847), an example in which anti-cancer activity is increased by a combination of an anti-cancer drug and a significant amount of gum arabic (Japanese Examined Patent Publication No. 3-127740), and an example in which the efficiency of transport of a drug (polypeptide) to specified cells is increased by synthesizing a complex of the drug and gum arabic (the specification of U.S. Pat. No. 5,554,386). However, there is not known method of stabilizing a useful protein, and no useful protein composition stabilized by mixing with gum arabic.

When a protein is used as a medical additive, particularly an additive for an injection drug, the additive itself is a heterogeneous protein for living organisms, and thus possibly causes allergy depending upon the amount of the additive added. Further, for gelatin derived from cattle and known as a protein which can be added to medicines for various purposes, it is difficult to securely avoid mixing with a protein which causes Bovine Spongiform Encephalopathy. As described above, various problems are pointed out. Therefore, there is demand for a compound other than protein, which is atoxic to living organisms, and which has the action to stabilize a protein. Known examples of such compounds include saccharides, polyhydric alcohols, and the like. However, it is difficult to stably maintain a biologically active protein in a storage form such as an aqueous solution or a freeze-dried solid in a wide pH range, and thus a stabilizer having higher safety and, efficacy is required.

DISCLOSURE OF INVENTION

As a result of intensive research, the inventors found that the activity of a protein can be stably maintained by mixing a useful protein and an aqueous solution of gum arabic having the basic structure of arabic acid. It was also found that a useful protein composition obtained by freeze-drying the mixture solution maintains high biological activity, leading to the achievement of the present invention.

Figure 1:
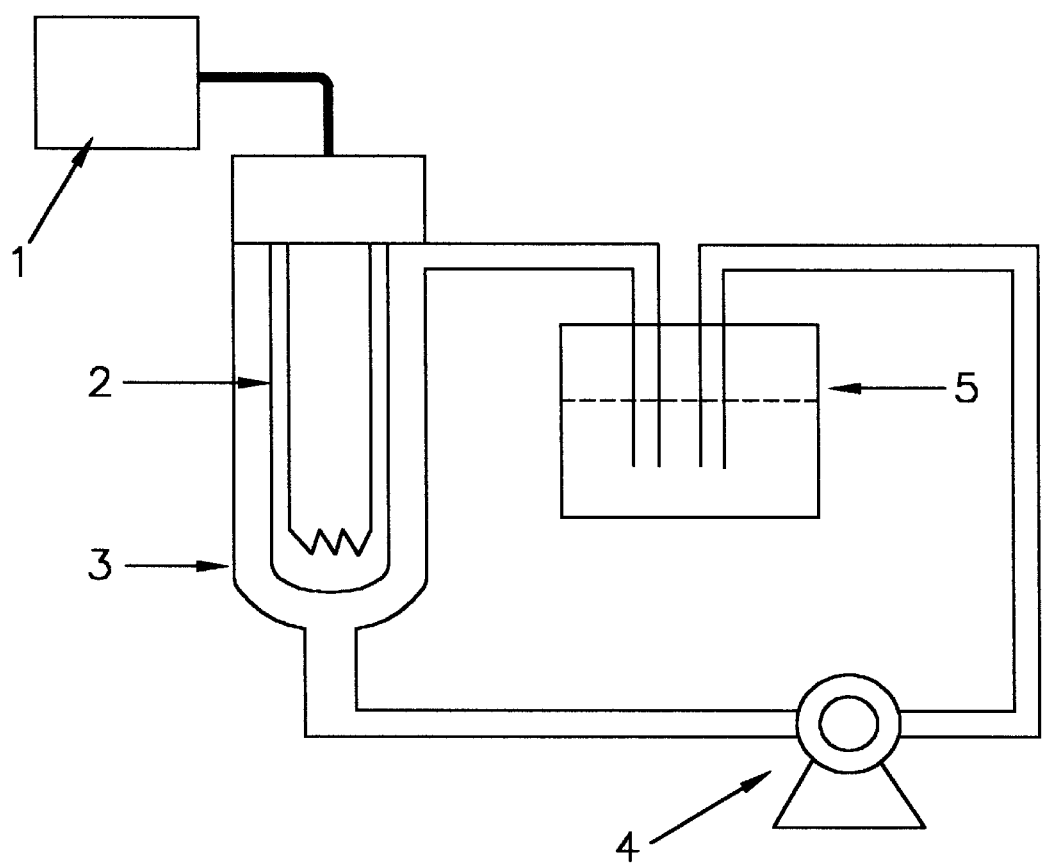
FIG. 1 is a drawing showing the construction of an ultraviolet irradiation apparatus used in the present invention.

Reference numerals 1 to 5 respectively denote the following:

1 body of ultraviolet irradiation apparatus
2 sterilization lamp
3 casing
4 pump
5 insect hemolymph containing baculoviruses

BEST MODE FOR CARRYING OUT THE INVENTION

The useful protein of the present invention is not limited, and any proteins can be used as long as the activity thereof is not inhibited by a compound having the basic structure of arabic acid. Examples of such proteins include enzymes and proteins having biological activity, for example, such as interferon, interleukin, insulin, growth hormone, G-CSF, erythropoeitin, NGF, and the like. Further examples include interferon derived from animals, such as canine interferon ($\alpha$, $\beta$, and $\gamma$ types), feline interferon-$\omega$, and the like.

For example, canine interferon-$\gamma$ is a polypeptide having the amino acid sequence shown in Reference 1. However, the useful proteins of the present invention also include polypeptides in which the amino acid sequences are partially substituted or deleted, or some amino acid residues are added, as long as they have the basic biological activity of interferon-γ for cells derived from dogs, for example, canine MDCK cells (ATCC CCL-34), as shown in Reference 2. An example of such polypeptides is a polypeptide composed of a maturation protein having the amino acid sequence shown by Sequence No. 3. Another example is canine interferon-γ composed of such a maturation protein as shown by Sequence No. 27 in which the sugar chain bond site is deleted.

Other examples include canine interferon-γ composed of such a maturation protein as shown by Sequence Nos. 28 and 29 in which the C terminal is deleted, and canine interferon-γ as shown by Sequence No. 30 in which an amino acid is added to the N terminal.

Although feline interferon is composed of a polypeptide having the amino acid sequence disclosed in U.S. Pat. No. 5,508,921, the useful proteins of the present invention also include polypeptides in which the amino acid sequences are partially substituted or deleted, or several amino acid residues are added.

The canine interferon-γ and feline interferon used in the present invention may be extracted from natural biomaterials and further purified to the required purity level, or may be chemically synthe sized. However, interferon produced by using the gene recombination technology can easily industrially be used. The useful proteins of the present invention can be produced by the gene recombination technology according g to the procedure of a conventional method. For example, the both e ends of a DNA fragment cording for a useful protein are digested with a restriction enzyme, and inserted into an appropriate region of a replicable plasmid, and the plasmid is introduced into cells in which it is sufficiently replicated.

DNA coding for the protein of canine interferon-γ required for producing canine interferon-γ by the gene recombination technology can be produced by, for example, the following method. Poly (A) RNA is extracted from canine cells, and converted into cDNA, and a gene coding for canine interferon-γ can be obtained by the polymerase chain reaction (abbreviated to "PCR" (hereinafter) using a primer based on a gene sequence coding for canine interferon-γ. An example of methods of obtaining RNA from canine lymphocytes stimulated by a mitogen is a conventional method using, for example, separation of polysome, sucrose density gradient centrifugation, or electrophoresis. As the method of extracting RNA from the canine cells, an appropriate method can be selected from methods including a guanidine thiocyanate-cesium chloride method (Reference 3) comprising guanidine thiocyanate treatment and then CsCl density gradient centrifugation, a method (Reference 4) comprising treatment with a surfactant using a vanadium complex in the presence of a ribonuclease inhibitor and then phenol extraction, a guanidine thiocyanate-hot phenol method, a guanidine thiocyanate-guanidine hydrochloride method, a guanidine thiocyanate-phenol chloroform method, a method comprising treatment with guanidine thiocyanate and then treatment with lithium chloride to precipitate RNA, and the like.

mRNA is isolated from the canine lymphocytes by a conventional method, for example, a lithium chloride/urea method, a guanidine isothiocyanate method, an oligo dT cellulose column method, or the like, and cDNA is synthesized from the thus-obtained mRNA by a conventional method, for example, the Gubler's method (Reference 5), the H. Oakayam's method (Reference 6), or the like. Although cDNA may be synthesized from the mRNA by basically using a reverse transcriptase such as avian osteoblast viruses (AMV), and partially using a primer in combination with a method using DNA polymerase, it is convenient to use a commercial synthetic or cloning kit. PCR using the cDNA as a template and the primer based on the base sequence of canine interferon-γ permits the production of DNA coding for the protein of canine interferon-γ.

DNA coding for the protein of feline interferon can easily be prepared from the plasmid pFeIFN1 disclosed in Japanese Unexamined Patent Publication No. 2-195884 using an appropriate restriction enzyme, for example, such as SfaN1 and Hinc II, according to the procedure of conventional gene recombination.

A synthetic plasmid as a expression plasmid vector in which the thus-obtained DNA is introduced into is introduced into, for example, simian COS cells to produce canine interferon-γ. Also DNA coding for the protein of canine interferon-γ is ligated to a expression vector of *Escherichia coli* so that canine interferon-γ producing *Escherichia coli* can be produced by transformation with the thus-obtained vector. In addition, a gene coding for the protein of canine interferon-γ is introduced into *Escherichia coli* having resistance to isoleucine antimetabolite and the ability to secrete the protein accumulated in the periplasm into a culture supernatant to accumulate canine interferon-γ in the culture supernatant. As *Escherichia coli* used for producing canine interferon-γ in the culture supernatant, any *Escherichia coli* bacteria can be used as long as they secrete periplasm proteins into the culture supernatant. *Escherichia coli* having the properties used in the present invention can be naturally obtained, but *Escherichia coli* having the above properties can easily be obtained by artificially obtaining a mutant according to the present invention. A parental strain for isolating a mutant is not limited, and any *Escherichia coli* strain can be used as the parental strain. However, for producing gene recombination proteins, HB101, JM101, JM105 and JM109 which are derived from *Escherichia coli* K-12 strain having excellent properties as a gene recombination host, BL21 strain derived from *Escherichia coli* B strain can be preferably used. As these *Escherichia coli* strains, commercial strains can be used. As the *Escherichia coli* used in the present invention, for example, TI41 strain (FERM P-16798) and TI139 strain (FERM P-16797), which are obtained from *Escherichia coli* JM101 strain, can be used. *Escherichia coli* TI41 and TI139 strains are obtained by conventional mutation method, and have resistance to thiaisoleucine. A mutant having resistance to isoleucine antimetabolite and the ability to secrete the protein accumulated in the periplasm into the culture supernatant can be induced by ultraviolet irradiation of a parental strain or treatment with a mutation inducer, for example, such as N-methyl-N'-nitro-N-nitrosoguanidine, ethyl methanesulfonate, or the like, and then obtaining a strain which can grow in a solid medium containing a concentration of isoleucine in which the parental strain cannot grow. Gram-negative enterobacteria belonging to Providenchia, Shipella, Serratia, and Citrobacter, which are close to *Escherichia coli* from the viewpoint of the taxonomy of microorganisms, are known to have periplasm as same as *Escherichia coli*, and highly similar thereto in genetic structure. Therefore, the same effects as the present invention can be possibly expected from enterobacteria having resistance to an isoleucine antimetabolite and the ability to secrete the protein accumulated in the periplasm into the culture supernatant.

As the isoleucine antimetabolite in the present invention, any substances may be used as long as they inhibit the growth of *Escherichia coli*, and the inhibition of growth is recovered by L-isoleucine, or they inhibit the activity of an isoleucine bi6synthetic enzyme or repress the expression of an enzyme gene, and the inhibition or repression is recovered by L-isoleucine. Examples of such substances include thiaisoleucine, isoleucine hydroxyamate, norleucine, α-aminobutylate, and the like. As these substances, commercially available substances can be used. Of these substances, thiaisoleucine is most preferably used.

In the present invention, a strain having the resistance to the isoleucine antimetabolite represents a strain which grows in a degree less decreased by the isoleucine antimetabolite than the parental strain. For example, at a concentration of isoleucine antimetabolite at which the parental strain shows a relative growth degree of 30% or less, a mutant showing a relative growth degree of 60% or more is preferably obtained. The relative growth degree is shown by a relative value of the measured absorbance of a culture solution at 660 nm to 100% of absorbance of a culture solution to which an isoleucine antimetabolite of each strain is not added.

Canine interferon-γ and feline interferon can also be produced by preparing recombinant Bombyx mori nuclear polyhedrosis viruses which infect Bombyx mori, using a Bombyx mori expression system. The recombinant Bombyx mori nuclear polyhedrosis viruses can be produced by co-transfection of Bombyx mori nuclear polyhedrosis virus DNA and a recombinant plasmid, which is produced by ligating DNA coding for the protein of feline interferon or canine interferon-γ to a cloning vector of Bombyx mori (Reference 7), into Bombyx mori established cells. Examples of such gene recombinant nuclear polyhedrosis viruses include rBNV100 to which DNA coding for the protein of feline IFN is recombined, rBNVγ to which DNA coding for the protein of canine IFN-γ is recombined.

rBNV100 can be produced by the method disclosed in Japanese Unexamined Patent Publication No. 4-207198. Namely, a recombinant plasmid is produced by a general gene operation technology in which DNA coding for the protein of feline IFN obtained from a plasmid extracted from a transformant of Escherichia coli deposited as FERM P-1633 in National Institute of Bioscience and Human Technology by a general method, is ligated to the downstream of a expression regulating portion of a Bombyx mori cloning vector, for example, such as pBM030 (Reference 7) or the like.

After co-transfection of the recombinant plasmid and Bombyx mori nuclear polyhedrosis virus DNA (Reference 7) into Bombyx mori established cells, for example, BM-N strain (Reference 7), by the method disclosed in this Reference, culture is continued, and then recombinant viruses are to cloned from non-recombinant (wild) viruses and recombinant viruses manifested in the culture solution by a general method such as a limiting dilution analysis or a plaque method to obtain recombinant nuclear polyhedrosis viruses. Since recombinant viruses has no ability to form polyhedra, they can easily be distinguished from wild viruses. rBNVγ can be obtained by the same method as rBNV100 using the recombinant plasmid obtained by joining DNA coding for the protein of canine interferon-γ to the downstream of a expression regulating portion of a Bombyx mori cloning vector such as pBM030.

Feline interferon or canine interferon-γ is produced by growing the recombinant nuclear polyhedrosis viruses in Bombyx mori established cells or Bombyx mori living organisms. In the use of the Bombyx mori established cells, BM-N cells are infected with a culture solution containing the recombinant viruses, and then cultured by plate culture or float culture. As a culture medium for culturing BM-N cells, for example, a TC-10 medium (Reference 8) containing fetal bovine serum (produced by Gibco Co., Ltd., and abbreviated to "FBS" hereinfater), and a TC-100 medium (produced by Nihon Nosan-kogyo Co., Ltd.) can be used. The culture temperature is preferably 25 to 28° C.

In the use of Bombyx mori organisms, a culture solution containing the recombinant viruses is injected into larvae of Bombyx mori which are then fed on artificial feed to produce feline interferon or canine interferon-γ in the hemolymph.

The stabilized useful protein composition disclosed in the present invention is expected to be used as a drug. Particularly, in producing a drug by the method of producing a useful protein using baculoviruses, it is necessary from the viewpoint of safety to inactivate the recombinant vaculoviruses used. For inactivating the recombinant Bombyx mori nuclear polyhedrosis viruses for producing a useful protein, it is necessary to lose the infectiosity of the baculoviruses and maintain the activity of the intended useful protein.

Inactivation of Bombyx mori nuclear polyhedrosis viruses which are baculoviruses is reported in detail by Watanabe et al. (Reference 9). However, a protein is denatured under physical inactivation conditions such as heating, ultraviolet rays, drying, or the like, and chemical inactivation conditions such as a bacteriocide such as phenol or formalin, alcohol, or the like, which are disclosed in this Reference, and it is thus difficult to use these conditions for producing a useful protein. This report also relates to inactivation of wild Bombyx mori nuclear polyhedrosis viruses, and does not disclose inactivation of recombinant Bombyx mori nuclear polyhedrosis viruses.

Japanese Unexamined Patent Publication No. 4-207198 discloses a method of inactivating recombinant Bombyx mori nuclear polyhedrosis viruses in which the pH of the Bombyx mori hemolymph is controlled to 0.5 to 3.0. This method is limited to production of a useful protein stable to acidity, and is thus not a satisfactory method. Japanese Unexamined Patent Publication No. 61-152276 discloses a technique for inactivating recombinant Escherichia coli using benzalkonium chloride, but does not disclose a method of inactivating recombinant baculoviruses. On the other hand, the inactivating action of benzalkonium chloride on viruses depends upon the types of viruses, and Yamamoto et al. report that HI viruses are inactivated by benzalkonium chloride (Reference 10). On the other hand, Watanabe et al. report that Flacherie viruses of Bombyx mori are not inactivated by benzalkonium chloride (Reference 11).

However, the present invention discloses that recombinant baculoviruses are inactivated by treatment with benzalkonium chloride without a loss of the biological activity of a useful protein, and discloses the method of stabilizing the useful protein obtained by benzalkonium chloride treatment, and a useful protein composition thereof.

Examples of quaternary ammonium salts used for inactivating recombinant baculoviruses include alkyl trimethylammonium salts, dialkyl dimethylammonium salts, alkyl dimethylbenzylammonium salts, alkyl pyridinium salts, acyl aminopropyldimethylbenzyl ammonium salts, and the like. Specifically, from the viewpoint of economy or safety, for example, benzalkonium chloride and benzetonium chloride are preferably used.

The concentration of the quaternary ammonium salt used is preferably a concentration sufficient for inactivating recombinant baculoviruses and causing no decrease in activity of the target useful protein. For example, the final concentration is preferably 0.01% by weight or more based on the culture supernatant of insect cultured cells infected with recombinant baculoviruses, or the hemolymph of *Bombyx mori* larvae infected with recombinant baculoviruses. However, the use of an excessively high concentration of quaternary ammonium salt is economically disadvantageous, and causes difficulties in purifying the target useful protein. Generally, treatment with 0.5% by weight or less of quaternary ammonium salt produces good results in the production of a useful protein.

Methods of treating the culture supernatant of *Bombyx mori* cells or the hemolymph of *Bombyx mori* with a quaternary ammonium salt include the method of adding a quaternary ammonium salt to the culture supernatant of *Bombyx mori* cells or the hemolymph of *Bombyx mori*, the method of adding the culture supernatant of *Bombyx mori* cells or the hemolymph of *Bombyx mori* to an aqueous quaternary ammonium salt solution, the method of immersing incised *Bombyx mori* directly in an aqueous quaternary ammonium salt solution, and the like. These methods produce the same effect. The temperature and time of treatment with a quaternary ammonium salt are not limited as long as the recombinant baculoviruses are sufficiently inactivated. For example, treatment at 0 to 25° C. for 1 to 24 hours produces good results.

Inactivation of the recombinant baculoviruses can also be achieved by ultraviolet irradiation. Ultraviolet irradiation for inactivating the recombinant baculoviruses may be performed at any one of wavelengths at which the baculoviruses can be inactivated. However, the wavelength is preferably 200 to 300 nm, more preferably 253.7 nm.

The ultraviolet irradiation apparatus used is preferably a flowing type. A preferred embodiment of the flowing type ultraviolet irradiation apparatus is described below with reference to the drawing.

FIG. 1 is a flowing type ultraviolet irradiation apparatus in accordance with an embodiment of the present invention. In FIG. 1, reference numeral 1 denotes the body of the ultraviolet irradiation apparatus.

The irradiation apparatus comprises a sterilization lamp 2 for ultraviolet irradiation, and a casing 3 to which the sterilization lamp 2 is mounted. Solution outlet and inlet are provided in the upper and lower portions of the casing so that the culture supernatant of *Bombyx mori* cells or the hemolymph of *Bombyx mori* flows between the sterilization lamp and the casing. When the temperature of the culture(s) supernatant of *Bombyx mori* cells or the hemolymph of *Bombyx mori* is increased due to ultraviolet energy during ultraviolet irradiation, the irradiation apparatus and the circulating line of the treatment solution are preferably cooled. A flow means (4) is provided in the circulating line. The distance of the sterilization lamp for ultraviolet irradiation and the casing depends upon the transmittance of the ultraviolet light applied, but it is preferably about 5 to 50 mm.

When the culture supernatant of *Bombyx mori* cells or the hemolymph of *Bombyx mori* is colored by denaturation due to bonding to a trace of metal or air oxidation, the transmittance of ultraviolet light is decreased, thereby causing difficulties in activating viruses. In order to prevent this phenomenon, a metal chelating agent is preferably added. As the metal chelating agent, disodium ethylenediaminetetraacetate is preferably used. The adding amount is preferably 0.1 to 100 mM, more preferably 1 to 10 mM, relative to a liquid to be treated.

The gene recombinant baculoviruses can also be inactivated by acid treatment at pH 3 or less, or alkali treatment at pH 9 or more. In this case, interferon-γ is inactivated, but the activity is reproduced by maintaining it neutral at a low temperature. The interferon-γ is inactivated, but the activity is reproduced by maintaining it neutral at a low temperature. The interferon-γ whose activity is reproduced as described above can be used for preparing the stabilized protein composition of the present invention. As the acid or alkali used for inactivating the gene recombinant baculoviruses, hydrochloric acid, sulfuric acid, acetic acid, phosphoric acid, formic acid, sodium hydroxide, and the like can be used, but the acid or alkali is not limited to these materials. The pH of the acid or alkali used is preferably a value sufficient for inactivating the gene recombinant baculoviruses, and is generally preferably 3 or less or 9 or greater, respectively. This method is preferably carried out at a temperature higher than the freeze point, preferably at 4 to 40° C. The treatment time is at least 1 minute, and treatment may be carried out for a longer time. Treatment for 1 to 12 hours produces good results.

The canine interferon-γ whose biological activity is lost by treatment can be treated under neutral conditions at a low temperature to reproduce the activity thereof. The neutral conditions preferably include a pH of 6 to 8, and the low temperature is preferably 0 to 15° C. The treatment time is preferably 12 hours or more, more preferably 1 to 7 days.

In the production of a useful protein using recombinant baculoviruses, the method of recovering the useful protein, for example, feline interferon or canine interferon-γ, from the culture supernatant of *Bombyx mori* cells or the larva hemolymph of *Bombyx mori* is not limited, and a general protein recovering method or purifying method can be used. Particularly, after the recombinant baculoviruses are inactivated with a quaternary ammonium salt, a useful protein, for example, feline interferon or canine interferon-γ, can be recovered by ultrafiltration. At the same time, by using an ultrafilter membrane which is not permeable to the recombinant baculoviruses, it is possible to recover the useful protein containing no inactivated recombinant baculoviruses from the permeated liquid side.

In ultrafiltration of the larva hemolymph of *Bombyx mori*, the hemolymph of *Bombyx mori* is colored brown with time, and a deterioration in filterability of ultrafiltration due to this coloring is recognized. Since the intended useful protein frequently has low stability, ultrafiltration is preferably carried out in as a short time as possible. In the present invention, it was found that coloring of the larva hemolymph of *Bombyx mori* is suppressed by maintaining at a pH 6 or less. Therefore, ultrafiltration at a pH 6 or less exhibits good filterability, and permits completion of ultrafiltration in a short time. However, even when the pH is lowered to 6 or less, coloring of the larva hemolymph of *Bombyx mori* begins at a pH or 7 or more, thereby deteriorating filtrability of ultrafiltration.

When the larva hemolymph of *Bombyx mori* infected with recombinant *Bombyx mori* nuclear polyhedrosis viruses, the pit must be set to 7 or more because of the need for a process for isolating and purifying the intended protein, and the stability thereof. It is effective to add a metal chelating agent.

Namely, the addition of the metal chelating agent causes no coloring of the larva hemolymph of *Bombyx mori* even at a pH of 7 or more, and thus enables maintenance of good filterability in ultrafiltration.

Examples of the metal chelating agent added to the larva hemolymph of *Bombyx mori* infected with recombinant *Bombyx mori* nuclear polyhedrosis viruses include; ethylenediamine tetraacetic acid (EDTA), ethylenediamine triacetic acid, ethylenediamine diacetic acid, trans-1,2- cyclohexanediamine tetraacetic acid, diethylenetriamine pentaacetic acid, triethylenetetramine hexaacetic acid, salts thereof, o-phenanthroline, diamines such as dipyridine, and the like. However, from the viewpoint of safety, EDTA is preferably used for producing a drug or the like. The concentration of the metal chelating agent used is not limited as long as coloring of the larva hemolymph of Bombyx mori is suppressed, but the addition of 2 mM or more of metal chelating agent generally effectively suppresses coloring of the larva hemolymph of Bombyx mori. The temperature of treatment with the metal chelating agent is not limited as long as the activity of the target protein is maintained, and the temperature is preferably 0 to 30° C.

The ultrafilter membrane used in ultrafiltration of the larva hemolymph of Bombyx mori infected with recombinant Bombyx mori nuclear polyhedrosis viruses is not limited, but industrially available ultrafilter membranes such as cellulose, polyphenylsulfone derivatives can preferably used. The shape of the ultrafilter membrane is also not limited, and commercially available ultrafilter membranes such as a plane ultrafilter membrane, a holofiber ultrafilter membrane, and the like can be used. In addition, various types of ultrafiltration devices can be used depending upon the ultrafilter membrane used, and the use of any one of ultrafiltration devices produces the same effect.

The ultrafilter membrane may have the molecular weight fraction ability to prevent permeation of the proteins occupying 80% to 90% of total proteins present in the larva hemolymph of Bombyx mori, which have molecular weights of about 30,000 and 70,000 in SDS-PAGE. Generally, an ultrafilter membrane having a molecular weight fraction size of 50,000 to 300,000, which is indicated as the performance of the ultrafilter membrane, can preferably be used. Further, it was unexpectedly found that an ultrafilter membrane having a molecular weight fraction size of 100,000 is less permeable to the proteins having molecular weights of about 30,000 and 70,000 in SDS-PAGE and present in the larva hemolymph of Bombyx mori. Therefore, when the target protein permeates an ultrafilter membrane having a molecular weight fraction size of 100,000, separation of the main contaminant proteins in the larva hemolymph of Bombyx mori and the intended protein can be sufficiently achieved on the permeated liquid side.

The method of isolating and purifying the useful protein produced by the gene recombination technology is not limited, and a general protein purifying method can be used. For example, the protein can be purified and isolated by a combination of chromatography using a silica gel carrier, an ion exchange carrier, a gel filtration carrier, a chelate carrier, a dye holding carrier, or the like, and ultrafiltration, gel filtration, dialysis, desalinization by salting out, or concentration.

The useful protein composition of the present invention can be produced by using the feline interferon or canine interferon-γ recovered and purified as described above.

The arabic acid used in the present invention has the following structure:

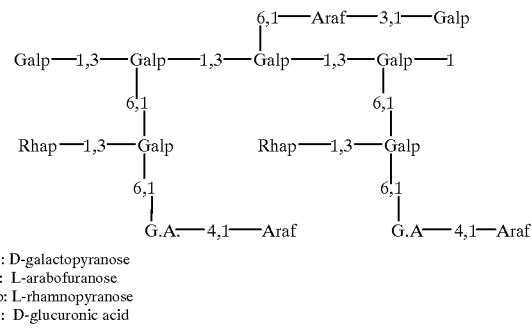

Galp: D-galactopyranose
Araf: L-arabofuranose
Rhap: L-rhamnopyranose
G.A.: D-glucuronic acid The compounds used for stabilizing proteins in the present invention and having the basic structure of arabic acid represent all compounds having the basic structure of arabic acid which contain, as a secondary component, no component which inactivates proteins or inhibits the stabilization action of arabic acid on proteins, and include gum arabic as a polymer compound (molecular weight of about 200,000 to 250,000) in which many arabic acid molecules are bonded, decomposed products and modified products thereof.

The concentration of an aqueous solution of a compound having the basic structure of arabic acid is any desired value, but a too low concentration has a low stabilizing effect, and a high concentration causes an increase in cost, and an increase in viscosity of gum arabic, thereby causing difficulties in handling. Therefore, the concentration is preferably 0.01 to 10% by weight, more preferably 0.5 to 2.0% by weight.

The biological activity of a useful protein is easily lost by external factors such as a temperature change due to freezing, melting, heating, or the like, a pH change due to extraction, purification, dissolution in a buffer, or the like. However, before these operations which induce inactivation, a useful protein is mixed with a compound having the basic structure of arabic acid in order to significantly maintain the biological activity of the useful protein.

It is generally known that as the purity of the intended protein increases with proceed of the purification steps of the operation of purifying the protein, the protein is easily inactivated. Namely, the purification operation is also an operation which induces inactivation, but inactivation of the protein due to purification can be prevented by mixing with a compound having the basic structure of arabic acid in a step before purification or in the course of purification.

Inactivation of a useful protein in an aqueous solution with time, i.e., inactivation in storage, can also be prevented by mixing with an aqueous solution of a compound having the basic structure of arabic acid. When a useful protein composition containing a compound having the basic structure of arabic acid is stored in a liquid state, it is preferably stored at 15° C. or less depending upon the thermal stability of the useful protein. The temperature is preferably as low as possible as long as the mixture is not frozen, and is preferably 4 to 10° C. In the case of long-term storage, the composition is preferably frozen or freeze-dried and then stored. In the case of freeze storage, the storage temperature is any low temperature which does not cause melting, and in the case of storage after melting, the conditions are the same as storage in a liquid state.

In the case of freeze drying, the preservation property increases as the water content decreases, and thus the composition is preferably dried to a moisture content of 5% or less. The thus-freeze-dried composition is preferably preserved in the dark and cool, and can be preserved at room temperature for one year and stably for a longer period of time in rifrigerated preservation. The thus-freeze-dried composition can be preserved for a 2 months and more under 50° C., cruel condition for preservation. In the use of the freeze-dried composition, it is disolved in water, in some cases, by a solution such as physiological saline. After dissolving, the preservation method is the same as the method of preservation in a liquid state.

The preferable pH of a mixture of the compound having the basic structure of arabic acid and the useful protein depends upon the pH stability of the useful protein itself, but the range of the pH stability of the useful protein is widened by mixing the useful protein and the compound having the basic structure of arabic acid. For example, an aqueous solution of IFN-γ used in the present invention is known to be significantly inactivated unless it is preserved at pH 6 to 8, but in the case of preservation of the mixture with an aqueous solution-of gum arabic, 100% of activity can be maintained in the pH range of 6 to 7, and 70% or more of activity can be maintained in the pH range of 4.5 to 8.0. In the case of freeze drying, approximately 100% of activity can be maintained in the pH range of 4.5 to 8.0.

The mixture of gum arabic and a useful protein can be used for various applications based on the function possessed by the protein. When a useful protein is advantageous for medical applications and a grade having no problem in medical applications, gum arabic of pharmacopeial grade or a grade for drug addition is used so that the mixture can be used for medical applications.

For enzymes used for various measurements and diagnoses other than medical applications, the stability can be improved by employing the stabilization method, preservation method and composition disclosed in the present invention, and thus such enzymes can be expected to be used for a long period of time.

Besides these components, the useful protein composition containing a compound having the basic structure of arabic acid can contain any one of compounds which do not inhibit the activity of proteins. For example, polyols such as polyethylene glycol, a surfactant such as Tween 20, saccharides such as sorbitol, amino acids such as glycine, or proteins such as gelatin may be added. Since the addition of salt causes no problem, osmotic pressure can be controlled by salt when the composition is used as an injection drug, for example.

EXAMPLES

Although the present invention will be described in detail below with reference to examples, the scope of the present invention is not limited to these examples.

Reference Example 1

Formation of Canine Interferon-γ Gene

A canine interferon-γ gene was prepared by the method disclosed in Japanese Unexamined Patent Publication No. 9-234085. Namely, the method comprises the following two steps:
(1) Preparation of canine cDNA Lymphocytes were separated from canine peripheral blood, and stimulated with phytohemagglutinin (PHA) for 48 hours at a final concentration of 50 µg/ml. After stimulation, entire RNA was prepared by using ISOGEN (produced by Nippon Gene Co., Ltd.). The thus-obtained RNA was dissolved in 10 mM of Tris hydrochloric acid buffer (pH 7.5) (abbreviated to "TE" hereinafter) containing 1 mM EDTA, and treated at 70° C. for 5 minutes, and then the same amount of TE containing 1M of LiCl was added. The RNA solution was applied to an oligo dT cellulose column equilibrated with TE containing 0.5 M LiCl, and then washed with the same buffer. After washing with TE containing 0.3 M LiCl, the poly (A) RNA adsorbed was eluted with 2mM EDTA (pH 7.0) containing 0.01% of SDS. Single stranded DNA was synthesized by using the thus-obtained poly (A) RNA. Namely, 5 µg of poly (A) RNA and 0.5 µg of oligo dT primer (12 to 18 mer) were placed in a 0.5-ml sterilized microcentrifuge tube and sterilized water treated with diethyl pyrocarbonate was added to a total of 12 µl. After incubation at 70° C. for 10 minutes, the tube was immersed in ice for 1 minute. A 200 mM Tris hydrochloric acid buffer (pH 8.4), 2 µl of 5000 mM KCL solution, 2 µl of 25 mM MgCl$_2$, 1 µl of 10 mM dNTP, and 2 µl of 0.1M DTT were added to the tube, followed by incubation at 42° C. for 5 minutes. Then, 1 µl of 200-unit reverse transcriptase (produced by Gibco BRL Co., Ltd., Super Script II) was added to the tube, and then further incubated at 42° C. for 50 minutes to effect cDNA synthetic reaction. After further incubation at 70° C. for 15 minutes, reaction was terminated, and the reaction solution was allowed to stand on ice for 5 minutes. To this reaction solution was added 1 µl of *E. coli* RNaseH (2 units/ml), followed by incubation at 37° C. for 20 minutes.

(2) Synthesis of canine interferon-γ gene

On the basis of the base sequences (Reference 1) of N and C terminals of canine interferon-γ, the following two primers were synthesized by a DNA synthesizer, in which a EcoRI site was added to the terminals.

5'GCGAATTCATGAATTATACAAGC-TATATCTTAGCT3' (Sequence No. 1)

5'GCGAATTCTTATTTCGATGCTCTGCGGC-CTCGAAA3' (Sequence No. 2)

2 µl of CDNA obtained above in (1) was added to each 0.5-ml microcentriefuge tube, and 20 pmol of each of the primers, a 20 mM Tris hydrochloric acid buffer (pH 8.0), 1.5 mM MgCl$_2$, 25 mM KCl, 100 µg/ml of gelatin, 50 µM of each dNTP, and 4-unit ExTaqDNA polymerase (produced by Takara Shuzo Co., Ltd.) were added to a total of 100 µl. 30 cycles of reaction were effected using a DNA thermal cycler produced by Perkin-Elmer Cetus Co., Ltd. under DNA denaturation conditions of 94° C. for 1 minute, primer annealing conditions of 55° C. for 2 minutes, and primer extension conditions of 72° C. for 3 minutes. The reaction solution was subjected to electrophoresis using 1% agarose gel to prepare DNA fragments of about 560 bp according to a conventional method (Reference 12). The DNA fragments were ligated to T-Vector produced by Invitrogen Co., Ltd. at 16° C. for 2 hours by using DNA Ligation Kit Ver. 1 produced by Takara Shuzo Co., Ltd. By using this product, *Escherichia coli* was transformed according to a general method, and plasmid DNA was prepared from the resultant transformant according to a general method. Next, it was confirmed by PCR under the same conditions as described above that PCR fragment was inserted into the plasmid. It was also confirmed by using a fluorescent DNA sequencer (DNA Sequencer 373S produced by Perkin-Elmer Co., Ltd.) and a diterminator cycle sequencing kit produced by Perkin-Elmer Co., Ltd. according to the attached protocol that the resultant DNA fragments have the base sequence (Sequence No. 3) of canine interferon-γ DNA.

Reference Example 2

Preparation of Expression Recombinant Plasmid Containing DNA Encoding Canine Interferon-γ

(1) Preparation of recombinant plasmid for animal cell expression

A preparation was made according to the method disclosed in Japanese Unexamined Patent Publication No. 9-234086. Namely, 1 μg of plasmid obtained in Reference Example 1 was digested with 30- units of the restriction enzyme EcoRI at 37° C. for 16 hours, and then subjected to electrophoresis using an agarose gel to prepare DNA fragments of canine interferon-γ of about 560 bp according to a conventional method.

On the other hand, 1 μg of cloning vector pCDL-SRα296 (Reference 13) was digested with 30-units of the restriction enzyme EcoRI at 37° C. for 16 hours, followed by dephosphorylation of the terminals using alkaline phosphatase (produced by Takara Shuzo Co., Ltd.) derived from bacteria. The product was then subjected to electrophoresisun using a 1% agarose gel to prepare DNA fragments of about 3.7 kp according to a general method. A litgation reaction was then effected at 160° C. for 16 hours using a DNA Litgation Kit Ver. 1 to joint the thus-prepared pCDL-SRα296 and canine interferon-γ DNA fragments. By using the resultant product, *Escherichia coli* HB101 was transformed according to a general method. 30 cycles of PCR was effected using two types of primers including a primer containing 27 bp from the initiating codon of DNA encoding canine interferon-γ, i.e., the following:

5' ATGAATTATACAAGCTATATCTTAGCT3' (Sequence No. 4); and a primer containing 30 bp on the downstream side of cloning site EcoRI of pCDL-SRα296, i.e., the following:

5'TTTTCACTGCATTCTAGTTGTGGTTTGTCC3' (Sequence No. 5)

under denaturation conditions of 94° C. for 1 minute, primer annealing conditions of 55° C. for 2 minutes, and primer extension conditions of 72° C. for 3 minutes using a DNA thermal cycler produced by Perkin-Elmer Cetus Co., Ltd. to obtain DNA fragments of about 650 bp. As a result, a plasmid was obtained in which DNA coding for canine interferon-γ was incorporated into pCDL-SRα296 in the positive direction. This recombinant plasmid was called pSRαγ. *Escherichia coli* containing this plasmid was named *E. coli* (pSRαγ).

(2) Preparation of recombinant plasmid for *Escherichia coli* expression

Preparation was made according to the method disclosed in Japanese Unexamined Patent Publication No. 9-234085. Namely, in order to obtain DNA coding for the maturation protein of canine interferon-γ, 30 cycles of PCR were conducted by using, as a template, the plasmid obtained in Reference Example 1 and two types of primers including a primer to which restriction enzyme NcoI site was added, i.e., the following:

5'CCGACCATGGCTCAGGCCATGTTTTT-TAAAGAAATAGAAAAC3'; (Sequence No. 6); and a primer to which restriction enzyme BamH1 site was added, i.e., the following:

5'GGATCCTTATTTCGATGCTCTGCGGC-CTCGAAACAG3' (Sequence No. 7)

under denaturation conditions of 94° C. for 1 minute, primer annealing conditions of 55° C. for 2 minutes, and primer extension conditions of 72° C. for 3 minutes by using a DNA thermal cycler produced by Perkin-Elmer Cetus Co., Ltd. to obtain DNA fragments of about 500 bp. The thus-obtained fragments were digested with 30-unit restriction enzyme NcoI, followed by precipitation with ethanol. Then, the fragments were digested with 30-unit restriction enzyme BamHI, and then subjected to electrophoresis using 1% agarose gel to prepare DNA fragments according to a general method.

Seperately, 1 μg of pET8c as an *Escherichia coli* expression vector was digested with 30-unit restriction enzyme NcoI. After precipitation with ethanol, the vector was digested with 30-units of the restriction enzyme BamHI, and then subjected to electrophoresis using a 1% agarose gel and was cut by BamHI to prepare DNA fragments according to a general method.

A litgation reaction was effected at 16° C. for 16 hours by using DNA Ligation Kit Ver. 1 to joint the pET8c prepared as described above and canine interferon-γ DNA fragments. By using the litgated product, *Escherichia coli* HB101 was transformed according to a conventional method. This *Escherichia coli* was named coli (pETγ).

Alternatively, preparation was made according to the method disclosed in Japanese Patent Application No. 10-167454. Namely, in order to obtain DNA coding for mature proteins of canine IFNγ, 30 cycles of PCR were conducted by using, as a template, cDNA obtained in Reference Example 1 and two types of primers including a primer to which the restriction enzyme EcoRI site was added, i.e., 5'-ACGTGGAATTCATGCAGGCCATGTTTTTTAAAG AA-3' (Sequence No. 8), and a primer to which the restriction enzyme HindIII site was added, i.e., 5'-CGAAGCTTCAAGATCTTTATTTCGATGCTCTGC GGCCTCGAAACAG-3' (Sequence No. 9), under denaturation conditions of 94° C. for 1 minute, primer annealing conditions of 55° C. for 2 minutes, and primer extension conditions of 72° C. for 3 minutes by using a DNA thermal cycler produced by Perkin-Elmer Cetus Co., Ltd. The thus-obtained fragments were subjected to electrophoresis using a 1% agarose gel to prepare DNA fragments of about 500 bp according to a conventional method (Reference 12).

The thus-obtained fragments were digested with 30-units of the restriction enzyme EcoRI, followed by precipitation with ethanol. Then, the fragments were digested with 30-units of the restriction enzyme Hind III, and then subjected to electrophoresis using a 1% agarose gel to prepare canine interferon-γ DNA fragments of about 500 bp according to a general method.

Seperately, 1 μg of pKK223-2 (produced by Pharmacia Co., Ltd.) as an *Escherichia coli* expression vector was digested with 30-units of the restriction enzyme EcoRI. After precipitation with ethanol, the vector was digested with 30-units of the restriction enzyme Hind III, and then subjected to electrophoresis using 1% agarose gel to prepare DNA fragments according to a general method.

A litgation reaction was effected at 16° C. for 16 hours by using DNA Ligation Kit Ver. 1to join the pKK223-3 and canine interferon-γ DNA fragments prepared as described avode. *Escherichia coli* HB 101 strain was transformed by a calcium chloride method. A transformant growing on a LB plate containing 100 μ/ml of ampicillin, a plasmid was extracted from the bacteria cultured in 3 ml of LB medium containing 100 μg/ml of ampicillin for 8 hours, and collected therefrom, purified, and then cut with restriction enzymes EcoRI and Hind III to obtain a plasmid for obtaining DNA fragments of about 500 bp. Thus-obtained recombinant plasmid was named pKK-γ, and *Escherichia coli* JM101, TI41 and TI139strains were transformed by using this plasmid according to a general method. These *Escherichia coli* strains were respectively named *Escherichia coli* JM101 (pKK-γ), *Escherichia coli* TI41 (pKK-γ) and *Escherichia coli* TI139 (pkk-γ).

(3) Preparation of plasmid for *Bombyx mori* expression

1 μg of vector pBM030 (Reference 7) was digested with 3units of the restriction enzyme EcoRI at 37° C. for 16 hours, and the termini were dephosphorylated with 1-unit of alkaline phosphatase (produced by Takara Shuzo Co., Ltd.) derived from bacteria. The resultant product was subjected to electrophoresisus using a 1% agarose gel to prepare DNA fragments of about 11.3 Kb according to a general method.

A ligation reaction was effected at 16° C. for 16 hours by, using DNA Ligation Kit Ver. 1 to joint the pBM030 prepared as described above and the canine interferon-γ DNA fragments prepared as described above in (2). By using the product, *Escherichia coli* HB101 strain was transformed. For the colonies growing on a LB plate containing 100 μg/ml of ampicillin, 30 cycles of PCR were conducted by using two types of primers including a primer containing 27 bp from the initiating codon of DNA coding for canine interferon-γ, i.e., the following:

5' ATCAACACGCACGAATCTAACGCT3' (Sequence No. 10); and a primer containing 26 bp on the downstream side of the cloning site EcoRI of pBM030, i.e., the following:

5' ATCAACAACGCACAGAATCTAACGAT3' (Sequence No. 11)

under DNA denaturation conditions of 94° C. for 1 minute, primer annealing conditions of 55° C. for 2 minutes, and primer extension conditions of 72° C. for 3 minutes by using a DNA thermal cycler produced by Perkin-Elmer Cetus Co., Ltd. to obtain DNA fragments of about 650 bp, to obtain a recombinant vector in which DNA coding for canine interferon-γ was inserted in pBM030 in the positive direction. The thus-obtained recombinant plasmid was named pBMγ. *Escherichia coli* containing this plasmid was named *E. coli* (pBMγ).

In addition, a *Bombyx mori* expression plasmid for canine interferon-γ mutant was prepared according to the method disclosed in Japanese Patent Application No. 10-160627. Namely, on the basis of the base sequences (Reference 1) of the N and C terminals of canine interferon-γ, Japan Bio Service Co., Ltd. was entrusted with synthesis of two types of primers including the following primers:

5'GCAGATCTATGAATTATACAAGC-TATATCTTAGCT3' (Sequence No. 12); and

5'GCGAATTCTTATTTCGATGCTCTGCGGC-CTAGGAAA3' (Sequence No. 2)

2 μl of cDNA obtained in Reference Example 1 was. placed in each of 0.5-ml microcentrifuge tubes, and 20 pmol of each primer, 10 mM Tris hydrochloric acid buffer (pH 8), 1.5 mM MgCl2, 25 mM KCl, 100 μg/ml of gelatin, 50 μM of each dNTP, and 4-unit ExTaqDNA polymerase (produced by Takara Shuzo Co., Ltd.) were added to each of the tubes to a total of 100 μl. 30 cycles of reaction were conducted under DNA denaturation conditions of 94° C. for 1 minute, primer annealing conditions of 55° C. for 2 minutes, and primer extension conditions of 72° C. for 3 minutes by using a DNA thermal cycler produced by In Perkin-Elmer Cetus Co., Ltd. The product was subjected to electrophoresis using a 1% agarose gel to prepare DNA fragments of about 517 bp (Sequence No. 13) according to a general method (Reference 12). The thus-obtained DNA fragments were joined to T-Vector produced by Invitrogen Co. according to a general method. By using the product, *Escherichia coli* was transformed according to a general method, and plasmid DNA was prepared from the resultant transformant according to a general method. Next, by using a fluorescent DNA sequencer (DNA sequencer 373S produced by Perkin-Elmer Co., Ltd.) according to the attached protocol, it was confirmed by using a di-terminator cycle sequencing kit produced by Perkin-Elmer Co., Ltd. that the obtained DNA fragments have the base sequence of DNA coding for canine interferon-γ.

Next, PCR was conducted by using a combination of three types of primers (Sequence Nos. 14 to 19) and the DNA fragments as a template under the same conditions as described above to obtain three types of PCR amplification fragments (Sequence Nos. 20 to 22). These fragments were recovered according to a general method, and then the fragments shown by Sequence Nos. 20, 21 and 22 were cut with restriction enzymes BamHI and EcoRV, restriction enzymes HincII and SnabI, and restriction enzymes EcoRV and EcoRI, respectively. The fragment shown by Sequence No. 19 treated with the restriction enzymes and the fragment shown by Sequence No. 22 treated with the restriction enzymes were mixed, and then inserted into the EcoRI and BamHI sites of pUC19 according to a general method to obtain a recombinant vector. The thus-obtained vector was cut with restriction enzyme EcoRV, and then the fragment shown by Sequence No. 21 was inserted into the vector according to a general method to obtain a recombinant vector. The base sequence of inserted DNA (Sequence No. 23) was confirmed by the same method as described above. Then, the inserted DNA was recovered by restriction enzymes BamHI and EcoRI, and inserted into pBM030 digested with restriction enzymes BglII and EcoRI to prepare *Bombyx mori* expression recombinant vector pBMγS2 (−). PCR was conducted by using pBMγS2(−) as a template, and primers shown by Sequence Nos. .24 and 25 to obtain DNA fragments shown by Sequence No. 26. The fragments were treated with a restriction enzyme by the same method as described above, and then inserted into BglII and EcoRI sites of pBM030 to prepare pBMγS2(−)/−20.

Reference Example 3

Preparation of Recombinant *Bombyx mori* Nuclear Polyhedrosis Virus Recombined with DNA Coding for Canine Interferon-γ

Recombinant viruses were produced according to the method of Reference 7. Namely, 2.5 ml of DNA mixture (containing 0.25 M CaCl$_2$, 10 μg of DNA of *Bombyx mori* nuclear polyhedrosis virus BmNPV T3 strains (Reference 7), and 65 μg of DNA of recombinant plasmid pYU871) was added dropwise to 2.5 ml of solution containing 50 mM HEPES buffer (pH 7.1), 0.28 M NaCl, 0.7 mM Na$_2$HPO$_4$, and 0.7 mM NaH$_2$PO$_4$. 0.5 ml of the resultant suspension was added to a culture medium of about 3×10$^5$Bm-N cells which were cultured by plate culture in a 5 ml of TC-10 medium (Reference 8) containing 10% FBS in a 25-cm$^2$ flask to introduce DNA into *Bombyx mori* cells. 20 hours after, the medium was changed by a new medium, followed by further culture for 7 days. Then, the culture solution was recovered, and centrifuged to obtain a clear supernatant. The supernatant was diluted, and then added to a culture medium of BM-N cells culture by plate culture. After culture for 8 days, a culture medium was selected, in which virus infection was observed by microscopic observation, and no polyhedron was formed (limiting dilution method).

The limiting dilution method was repeated seven times to clone recombinant viruses. Here, recombinant viruses containing DNA (Sequence No. 23) coding for canine IFN-γ mutant was named rBNVγS2(-), and recombinant viruses containing DNA (Sequence No. 3) coding for canine IFN-γ was named rBNVγ.

Reference Example 4

Preparation of Recombinant *Bombyx mori* Nuclear Polyhedrosis Virus Containing DNA Cording for Feline IFN (1) Preparation of gene fragment coding for feline IFN Recombinant *Bombyx mori* nuclear polyhedrosis viruses containing DNA coding for feline IFN were produced from plasmid pFeIFN1 (Japanese Unexamined Patent Publication No. 2-195884) according to the method disclosed in Japanese Unexamined Patent Publication No. 4-207198. Namely, SfaNl-Hinc II fragments containing a feline IFN gene obtained from pFeIFN1 were introduced into pUC18, and then cut out as BamHl-HincII fragments referred to as feline IFN gene.

(2) Preparation of *Bombyx mori* expression plasmid

The Bam HI-HincII fragments were inserted into Bgl II-Hinc II sites of *Bombyx mori* cloning vector pBM030 (Reference 7) to obtain plasmid pYU871.

(3) Preparation of recombinant *Bombyx mori* nuclear polyhedrosis viruses recombined with DNA coding for feline IFN Recombinant viruses were produced by the method of Reference 7. Namely, 2.5 ml of DNA mixture (containing 0.25 M $CaCl_2$, 10 μg of DNA of *Bombyx mori* nuclear polyhedrosis virus BmNPV T3 strains (Reference 7), and 65 μg of DNA of recombinant plasmid pYU871) was added dropwise to 2.5 ml of solution containing 50 mM HEPES buffer (pH 7.1), 0.28 M NaCl, 0.7 mM $Na_2HPO_4$, 0.7 mM $NaH_2PO_4$. 0.5 ml of the resultant suspension was added to a culture medium of about $3 \times 10^5$ BmN cells which were cultured by plate culture in a 5 ml of TC-10 medium (Reference 2) containing 10% FBS in a 25-$cm^2$ flask to introduce DNA into *Bombyx mori* cells. 20 hours after, the medium was changed by a new medium, followed by further culture for 7 days. Then, the culture solution was recovered, and centrifuged to obtain a clear supernatant. The supernatant was diluted, and then added to a culture medium of BM-N cells cultured by plate culture. After culture for 8 days, a culture medium was selected, in which virus infection was observed by microscopic observation, and no polyhedron was formed (limiting dilution method).

The limiting dilution method was repeated seven times to clone recombinant viruses. Here, recombinant viruses containing DNA coding for feline IFN was named rBNV100.

Reference Example 5

Preparation of rBNVγ, rBNVγS2(-) and rBNV100 Virus Solutions

50 μl of culture solution of BM-N cells containing the recombinant viruses cloned in Reference Example 3 or 4 was added to about $3 \times 10^5$ Bm-N cells cultured by plate culture in a 15 ml of TC-10 medium containing 10% FBS at the bottom of a 75-$cm^2$ flask. After culture at 27° C. for 5 days, the culture solution was centrifuged at 3,000 rpm for 5 minutes. The resultant centrifugal supernatant was used as each of rBNVγ, rBNVγS2(-) and rBNV100 virus solutions. The resultant recombinant virus solution was diluted 10 to 7 times, and 1 ml of the diluted solution was added to a culture solution of BM-N cells, followed by culture at 27° C. for 7 days. As a result, virus infection without formation of nuclear polyhedra was observed by microscopic observation, and it was thus confirmed that recombinant viruses were obtained.

Reference Example 6

Activity Measurement Method

The activity of interferon was measured by an antiviral action. For canine interferon-γ, activity was also measured by the expression enhancing action of canine cell strain class II MHC.

The antiviral activity was measured by the CPE method according to Reference 14. Vesicular Stomatitis viruses were used as measurement viruses, canine MDCK (ATCC CCL-34) cells were used as sensitive cells for measuring the antiviral activity of canine IFN-γ, and feline FC9 (Reference 15) cells were used as sensitive cells for measuring the antiviral activity of feline IFN. Namely, a diluted solution of a sample containing canine IFN-γ was added to canine MDCK (ATCC CCL-34) cells which were cultured at 37° C. to confluence on a 96-well micro plate, or similarly, a diluted solution of a sample containing feline IFN was added to feline FC9 cells which were cultured at 37° C. to confluence, followed by further culture at 37° C. for 20 to 24 hours to induce antiviral activity. After VSV was added, culture was conducted at 37° C. for 24 hours, and then the canine MDCK cells or feline FC9 cells, which lived on the micro plate and adhered thereto, were stained with a crystal violet stain containing 20% formalin. The amount of crystal violet on the micro plate was measured by measuring absorbance at 570 nm to determine the amount of canine IFN-γ or feline IFN when 50% of cells were kept alive. This amount of canine IFN-γ or feline IFN was defined as one unit (1U) of antiviral activity. The standard deviation of antiviral activity data obtained by the above method was 32%.

Cell strain FCBR1 derived from canine mammary tumor tissue which manifested class II MHC was established according to the method disclosed in Reference 16. By using this strain, the expression enhancing action of class II MHC was measured. $1 \times 10^4$ cells of FCBR1 were adhered to each of the wells of a 24-well plate, and expressed canine interferon-γ was added to the cells, followed by culture under the condition of 5% $CO_2$ at 37° C. overnight. After culture, the cells were separated by trypsin, and then centrifuged in a 1.5-ml microcentrifuge tube. To this tube was added 10 μl of rat anti-canine MHC class II monoclonal antibody (produced by Stratagene Co., Ltd.). After suspension with 50 μl of a ERDF medium (produced by Kyokuto Seiyaku Co., Ltd.) containing 10% FBS, the suspension was allowed to stand on ice for 1 hour. After washing with PBS, the solution was suspended with 5 μl of FITC-labeled rabbit anti-rat monoclonal antibody (produced by Stratagene Co., Ltd.) and 50 11 of ERDF medium containing 10% FBS, and then allowed to stand on ice for 1 hour. After washing with PBS, analysis was made by FAC Scan produced by Becton Dickinson Co., Ltd.

Reference Example 7

Production of Canine Interferon-γ Using COS-1 Cells

5 μg of pSRay obtained in Reference Example 2 was added to 4 ml of ERDF medium containing 50 mM Tris hydrochloric acid buffer (pH 7.5), 400 μg/ml of DEAE dextran (Pharmacia Biotech Co., Ltd.) and 100 μM chlorokin (Sigma Co., Ltd.), to which 10% FBS was added. COS-1 cells (ATCC CRL-1650), which were grown to 50% confluence in an ERDF medium containing 10% FBS using a dish having a diameter of 10 cm, were washed once with PBS. 4 ml of the DNA mixture obtained as described above was added to the cells, followed by culture under the condition of 5% $CO_2$ at 37° C. Four hours after, the cells were washed with PBS, and then cultured in 20 ml of ERDF medium containing 10% FBS under the condition of 5% $CO_2$ at 37° C. for 4 days to obtain a culture supernatant in which canine interferon-γ was produced. As a result of measurement of the antiviral activity of the thus-obtained culture supernatant, activity of $10^4$ dilution units/ml or more was observed.

Reference Example 8

Production of Canine Interferon-γ Using Escherichia coli

A single colony of E. coli (pETγ) obtained in Reference Example 2 was inoculated into 5 ml of LB medium containing 100 μg/ml of ampicillin. After culture was performed at 37° C. until $OD_{600}$ was about 0.7, isopropyl-β-D-thiogalactopyranoside (IPTG) at a final concentration of 0.5 mM was added to the culture medium, followed by further culture for 1.5 hours.

1.5 ml of culture solution was placed in a 1.5-ml microcentrifuge tube, and centrifuged at 12000 rpm for 5 minutes. After the supernatant was removed, the residue was suspended in 1.5 ml of Tris hydrochloric acid buffer (pH 7.5), and the cells were crushed on ice by using Handy Sonic. The cells were centrifuged at 20000 rpm for 30 minutes to obtain a soluble fraction (supernatant).

As a result of measurement of the antiviral activity of this fraction, activity of $10^7$ dilution units/ml or more was observed. Also, measurement of the expression enhancing action of class II MHC showed an increase of 100% in expression of class II MHC on canine mammary tumor cell strain FCBR1.

Reference Example 9

Production of Canine Interferon-γ in Culture Supernatant of Escherichia Coli

Mutants secreting a protein accumulated in the periplasm into a culture supernatant were isolated by isolating a thiaisoleucine-resistant strain, and then screening mutants having the ability to secrete, alkaline phosphatase as one of Escherichia coli periplasm proteins from the obtained resistant strains.

a) Isolation of thiaisoleucine-resistant mutants

Cells of Escherichia coli JM101, JM105 and BL21 which were cultured in 5 ml of a LB medium (polypeptone 10 g/l, yeast extract 5 g/l, NaCl 5 g/l) at 37° C. up to the logarithmic growth phase were recovered, and washed twice with physiological saline. 5 ml of malic acid buffer (pH 6.0) containing 250 μg/ml of N-methyl-N'-nitro-N-nitroguandine was added to the cells to form a suspension. After the suspension was then kept at 37° C. for 5 minutes, the cells were recovered by centrifugation, and then washed twice with physiological saline.

The thus-obtained cells were appropriately diluted, and spread on a plate medium shown in Table 1 to which each of various concentrations of 0.1 to 2.0 mM of thiaisoleucine (produced by Sigma Co., Ltd.) was added, followed by culture at 37° C. for one week. The grown colonies were streaked again on a plate containing the same concentration of thiaisoleucine, and single colonies were isolated to obtain about 250 mutants for each Escherichia coli strain.

TABLE 1

| Basic medium for separating thiaisoleucine-resistant strain | |
|---|---|
| $Na_2HPO_4$ | 12.8 g |
| $KH_2PO_4$ | 3.0 g |
| NaCl | 0.5 g |
| $NH_4Cl$ | 1.0 g |
| Glulose* | 5.0 g |
| L-proline* | 0.1 g |
| Thiamine* | 20 mg |
| $MgCl_2$* | 10 mM |
| $CaCl_2$* | 1 mM |
| Agar* | 20.0 g |

*added aseptically after separate sterilization b) Separation of alkaline phosphatase secreting strain A plate medium (Table 2) in which the phosphoric acid concentration was kept at 3.0 mM or less was prepared, each of all isolated thiaisoleucine-resistant strains, and parental strains as reference controls (JM101, JM105 and BL21) was streaked on the plate medium, followed by culture at 37° C. overnight. Equivalents of 1% agar (cooled to about 60° C.) and 50 mM Tris-HCl (pH 9.0) containing 1.28 mg/ml of p-nitrophenyl phosphate and 10 MM $MgCl_2$ were mixed, and the resultant mixture was overlaid on the plate medium before the mixture hardened. The medium was then kept at 37° C. for 1 hour to obtain 18 strains in which a colony was more yellowed, as compared with the parental strains.

Of these strains, two strains derived from JM101 were respectively referred to as TI41 (FERM P-16798) and TI139 (FERM P-16797)

TABLE 1

| Basic medium for screening alkaline phosphatase secreting variant | |
|---|---|
| $Na_2HPO_4$ | 0.4 g |
| $KH_2PO_4$ | 0.9 g |
| NaCl | 0.5 g |
| $NH_4Cl$ | 1.0 g |
| Glulose* | 5.0 g |
| L-proline* | 0.1 g |
| Thiamine* | 20 mg |
| $MgCl_2$* | 10 mM |
| $CaCl_2$* | 1 mM |
| Agar* | 20.0 g |

*added aseptically after separate sterilization c) Resistance of thiaisoleucine-resistant variant Escherichia coli strains JM101, TI41 and TI139 were shake-cultured at 30° C. for 24 hours by using the medium shown in Table 1, and the cells which grew were washed with physiological saline. A suspension of the washed bacterial cells was inoculated into 5 ml of medium shown in Table 1 containing 20 mg/l of L-thiaisoleucine, followed by shaking culture at 30° C. for 48 hours. Then, the degree of growth of each strain was examined by measuring absorbance at 660 nm. As a result, it was found from Table 3 that growth of thiaisoleucine-resistant strains TI41 and TI139 used in the present invention is not inhibited by thiaisoleucine, thereby exhibiting high resistance to thiaisoleucine, as compared with parental strain JM101.

TABLE 3

Comparison of resistance to thiaisoleucine

| | Relative degree of growth (%) | |
|---|---|---|
| Strain | No addition of thiaisoleucine | Addition of 20 mg/l of thiaisoleucine |
| Escherichia coli TI41 (Example of this invention) | 100 | 95.2 |
| Escherichia coli TI139 (Example of this invention) | 100 | 106.1 |
| Escherichia coli JM101 (Comparative Example | 100 | 17.1 |

(2) Secretory production of canine interferon-γ using *Escherichia coli*

A single colony of each of *Escherichia coli* JM101 (pKK-γ), TI41 (pKK-γ) and TI139 (pKK-γ) obtained in Reference Example 2 was inoculated into 5 ml of LB medium containing 100 μg/ml of ampicillin. After culture at 37° C. was conducted until $OD_{600}$ was about 0.7, isopropyl-β-D-thiogalactopyranoside (IPTG) at a final concentration of 1 mM was added to the culture solution, followed by further culture for 16 hours. 1.5 ml of the culture solution was placed in a 1.5-ml microcentrifuge tube, and then centrifuged at 9,000 rpm for 5 minutes to obtain a culture supernatant. The results of measurement of the antiviral activity of the culture supernatant are shown in Table 4. These results indicate that the use of *Escherichia coli* TI41 or TI139 strain as a host causes accumulation of a large amount of canine interferon-γ in the culture supernatant.

TABLE 4

Secretory production of canine interferon-γ in culture supernatant.

| Strain | IFN-γ activity in culture supernatant (U/ml) |
|---|---|
| *Escherichia coli* TI41 (pKK-γ) (Example of this invention) | $3.4 \times 10^5$ |
| *Escherichia coli* TI139 (pKK-γ) (Example of this invention) | $5.9 \times 10^5$ |
| *Escherichia coli* JM101 (pKK-γ) (Comparative Example) | $2.1 \times 10^4$ |

*Escherichia coli* TI139 (pKK-γ) was inoculated into 400 ml of LB medium, and aerobically cultured at 37° C., and 1 mM IPTG was added to the culture solution in the logarithmic growth phase. After culture was continued, 5 ml of culture solution was collected after an elapse of each of 3 hours, 5 hours, 8 hours and 21 hours. Each of the culture solutions was centrifuged at 9,000 for 5 minutes to separate the culture supernatant and cells. The cells were suspended in 5 ml of 20 mM sodium phosphate buffer (pH 7.0), completely crushed on ice by ultrasonic waves, and then centrifuged at 12,000 rpm to obtain a supernatant as a soluble fraction of cells.

The results of measurement of antiviral activities of the thus-obtained culture supernatant and soluble cell fraction are shown in Table 5. The results indicate that in the *Escherichia coli* mutants of the present invention, canine interferon-γ is mostly secreted to the outside of the cells 21 hours after culture.

TABLE 5

Change with time in distribution of canine interferon-γ in *Escherichia coli*

| Culture time (h) | IFN activity in culture supernatant (U/ml) | IFN activity in soluble fraction (within cells) (U/ml) |
|---|---|---|
| 3 | $4.14 \times 10^3$ | $3.01 \times 10^5$ |
| 5 | $8.64 \times 10^3$ | $1.01 \times 10^6$ |
| 8 | $5.44 \times 10^4$ | $9.01 \times 10^5$ |
| 21 | $8.56 \times 10^5$ | $5.00 \times 10^4$ |

Reference Example 10

Production of Canine Interferon-γ Using *Bombyx mori* Established Cells 0.5 ml each of virus solution of the recombinant virus BNVγ obtained in Reference Example 3 was added to about $3 \times 10^6$ BmN cells which were cultured in plate culture in a TC-10 medium containing 10% FBS in a 25-cm² flask. 30 minutes after, the medium was changed by 5 ml of new TC-10 medium containing 10% FBS, followed by culture at 27° C. for 3 days. The centrifugal supernatant of the culture solution was collected to measure activity. As a result, antiviral activity of $10^5$ U/ml was obtained.

Reference Example 11

Production of Canine Interferon-γ in *Bombyx mori* Living Organisms

Larvae of *Bombyx mori* in the fifth stage and second day were injected with 50 μl/body of virus solution of the recombinant virus rBNVγ or rBNVγS2 (−) obtained in Reference Example 3, and fed on commercial artificial feed (produced by Kanebo Silk Elegance Co., Ltd.) at 25° C. for 4 days. Then, the abdomens of 10 larvae were incised, and the hemolymph was collected into an Eppendorf tube ice-cooled, and then centrifuged to obtain a supernatant. After filtration with 0.22 μm-filter and sterilization, activity was measured. As a result, the antiviral activity of the *Bombyx mori* hemolymph was about $2 \times 10^7$ U/ml when rBNVγ was used, while when rBNVγS2 (−) was used, the antiviral activity of the *Bombyx mori* hemolymph was about $4 \times 10^7$ U/ml, which was twice as high as rBNVγ. Also, as a result of measurement of the expression enhancing action of class II MHC of the *Bombyx mori* hemolymph obtained by inoculating rBNVγ, the amount of expression of class II MHC on canine mammary tumor cell strain FCBR1 was increased by 100%.

Reference Example 12

Determination of Virus Concentration by Cytopathogenic Effect

A cultured cell supernatant or hemolymph of *Bombyx mori* infected with recombinant *Bombyx mori* nuclear polyhedrosis viruses was diluted, and added to a culture solution of $5 \times 10^5$/ml of BM-N cells. After culture at 27° C. for 10 days, the cytopathogenic effect on the BM-N cells was recognized by microscopic observation to calculate the amount of infectious viruses. The amount of infectious viruses was determined by determining TCID50 (50% tissue culture infectious dose) according to Reference 17.

Reference Example 13

Production of Canine IFN-γ in *Bombyx mori* Living Organisms and Inactivation of Recombinant *Bombyx mori* Nuclear Polyhedrosis Virus by Benzalkonium Chloride Larvae of *Bombyx mori* in the fifth stage and second day were injected with 2 μl/body of virus solution of the recombinant virus rBNVγ obtained in Reference Example 3, and fed on commercial artificial feed (Kanebo Silk Elegance Co., Ltd.) at 25° C. for 4 days. The abdomens of 10 larvae were incised, immersed in 100 ml of 50 mM acetic acid buffer (pH 3.5) containing 0%, 0.01% or 0.02% benzalkonium chloride, and then maintained at 4° C. for 20 hours. The resulting extract of *Bombyx mori* hemolymph was centrifuged at 5,000 rpm for 15 minutes to recover the supernatant. The antiviral activity, protein concentration, and amount of infectious recombinant *Bombyx mori* nuclear polyhedrosis viruses of the resultant supernatant were examined. The results are shown in Table 6.

TABLE 6

Production of canine IFN-γ in *Bombyx mori* larvae and inactivation of recombinant *Bombyx mori* nuclear polyhedrosis viruses by behzalkonium chloride

| Experimental Example | Concentration of benzalkonium chloride (%) | Amount of infectious viruses (TCID$_{50}$/ml) | Antiviral activity (U/ml) | Protein Concentration (mg/ml) | Specific activity (U/mg protein) |
| --- | --- | --- | --- | --- | --- |
| Comp. Example | 0 | $8.6 \times 10^8$ | $1.4 \times 10^6$ | 12.5 | $1.1 \times 10^5$ |
| Example 1 of this invention | 0.01 | Not detected | $4.0 \times 10^6$ | 7.1 | $5.6 \times 10^5$ |
| Example 2 of this invention | 0.02 | Not detected | $2.0 \times 10^6$ | 6.6 | $3.0 \times 10^5$ |

Reference Example 14

Production of Feline IFN in *Bombyx mori* Living Organisms and Inactivation of recombinant *Bombyx mori* Nuclear Polyhedrosis Virus by Benzalkonium Chloride Larvae of *Bombyx mori* in the fifth stage and second day were injected with 2 μl/body of virus solution of the recombinant virus rBNV100 obtained in Reference Example 4, and fed on commercial artificial feed (Kanebo Silk Elegance Co., Ltd.) at 25° C. for 4 days. The abdomens of 10 larvae were incised, immersed in 100 ml of 50 mM acetic acid buffer (pH 3.5) containing 0%, 0.01% or 0.02% benzalkonium chloride, and then maintained at 4° C. for 20 hours. The resulting extract of *Bombyx mori* hemolymph was centrifuged at 5,000 rpm for 15 minutes to recover the supernatant. The antiviral activity, protein concentration, and amount of infectious recombinant *Bombyx mori* nuclear polyhedrosis viruses of the resultant supernatant were examined. The results are shown in Table 7.

TABLE 7

Production of feline IFN in *Bombyx mori* larvae and inactivation of recombinant *Bombyx mori* nuclear polyhedrosis viruses by behzalkonium chloride

| Experimental Example | Concentration of benzalkonium chloride (%) | Amount of infectious viruses (TCID$_{50}$/ml) | Antiviral activity (U/ml) | Protein Concentration (mg/ml) | Specific activity (U/mg protein) |
| --- | --- | --- | --- | --- | --- |
| Comp. Example | 0 | $8.6 \times 10^8$ | $7.0 \times 10^6$ | 11.7 | $5.9 \times 10^5$ |
| Example 1 of this invention | 0.01 | Not detected | $6.5 \times 10^6$ | 7.7 | $8.6 \times 10^5$ |

TABLE 7-continued

Production of feline IFN in *Bombyx mori* larvae and inactivation of recombinant *Bombyx mori* nuclear polyhedrosis viruses by behzalkonium chloride

| Experimental Example | Concentration of benzalkonium chloride (%) | Amount of infectious viruses (TCID$_{50}$/ml) | Antiviral activity (U/ml) | Protein Concentration (mg/ml) | Specific activity (U/mg protein) |
| --- | --- | --- | --- | --- | --- |
| Example 2 of this invention | 0.02 | Not detected | $6.1 \times 10^6$ | 6.1 | $1.0 \times 10^5$ |

Reference Example 15

Inactivation of Recombinant *Bombyx mori* Nuclear Polyhedrosis Virus by Benzethonium Chloride Larvae of *Bombyx mori* in the fifth stage and second day were injected with 2 μl/body of virus solution of the recombinant virus rBNVγ obtained in Reference Example 3, and fed on commercial artificial feed (Kanebo Silk Elegance Co., Ltd.) at 25° C. for 4 days. The abdomens of 10 larvae were incised, immersed in 100 ml of 50 mM acetic acid buffer (pH 3.5) containing 0%, 0.01% or 0.02% benzethonium chloride, and then maintained at 4° C. for 20 hours. The resulting extract of *Bombyx mori* hemolymph was centrifuged at 5,000 rpm for 15 minutes to recover the supernatant. The amount of infectious recombinant *Bombyx mori* nuclear polyhedrosis viruses of the resultant supernatant was examined. The results are shown in Table 8.

TABLE 8

Inactivation of recombinant *Bombyx mori* nuclear polyhedrosis virus by benzethonium chloride

| Experimental Example | Concentration of benzethonium chloride (%) | Amount of infectious viruses (TCID$_{50}$/ml) |
| --- | --- | --- |
| Comparative Example | 0 | $8.6 \times 10^8$ |
| Example 1 of this invention | 0.01 | Not detected |
| Example 2 of this invention | 0.02 | Not detected |

Reference Example 16

Production of Canine IFN-γ in *Bombyx mori* Living Organisms and Inactivation of Recombinant *Bombyx mori* Nuclear Polyhedrosis Virus by UV Irradiation Larvae of *Bombyx mori* in the fifth stage and second day were injected with 2 μl/body of virus solution of the recombinant virus rBNVγ obtained in Reference Example 3, and fed on commercial artificial feed (Kanebo Silk Elegance Co., Ltd.) at 25° C. for 4 days. The abdomens of 80 larvae were incised, and the hemolymph of each larva was extracted with 10 ml of cooled water containing 2.5 mM/l of sodium ethylenediaminetetraacetate. 800 ml of hemolymph extract was sent to the ultraviolet irradiation apparatus shown in FIG. 1 to irradiate the extract with ultraviolet rays with rated output of 7W at 253.7 nm by using the sterilization lamp. The maximum distance from the sterilization lamp was 10 mm, and the hemolymph extract was circulated with a convection time of 3 minutes to irradiate the extract with ultraviolet rays. As a result of measurement of ultraviolet transmittance of the hemolymph extract by using a spectrophotometer (Hitachi U-2000), the transmittance was 26% (10 mm cell).

After 1 hour and 2.5 hours, the hemolymph extract was sampled, and cultured together with *Bombyx mori* cells according to the method of Reference Example 12 to examine growth of viruses. In the hemolymph extract sampled 1 hour after (in consideration of the convection time, the actual irradiation time of ultraviolet rays was 0.4 hour), 75% of viruses were inactivated. In the hemolymph extract sampled 2.5 hours after (in consideration of the convection time, the aqtual irradiation time of ultraviolet rays was 1 hour), 100% of viruses were inactivated. As a result of measurement of the titer of canine interferon by a bioassay method according to the method of Reference Example 6, the titer was $3 \times 10^6$ U/ml.

Reference Example 17

Preparation of Canine Interferon-γ Using *Bombyx mori* Larvae

*Bombyx mori* larvae in the fifth stage and second day was inoculated with a virus solution of gene recombinant baculoviruses rBNVγ disclosed in Japanese Unexamined Patent Publication No. 9-234085, and feed on commercial artificial feed (Kanebo Silk Elegance Co., Ltd.) at 25° C. for 4 days. The abdomens of 50 larvae were incised, immersed in 500 ml of 50 mM phosphoric acid buffer (pH 3.5) containing 0.01% benzalkonium chloride, and then maintained at 4° C. for 20 hours. The resultant *Bombyx mori* hemolymph extract was neutralized with 2N NaCl, and then centrifuged at 5000 rpm for 15 minutes to recover a supernatant. The thus-obtained supernatant was poured into sulfopropyl cellulose (high performance type, produced by Pharmacia Co., Ltd.), and washed with a 20 mM phosphoric acid buffer (pH 7.0). The adsorbate was then eluted with sodium chloride at a linear concentration gradient, and a fraction having antiviral activity was collected. Canine IFN-γ was recovered, dialyzed overnight in a 20 mM sodium phosphate buffer (pH 7.0), and then used as a canine IFN-γ sample for examining a stabilizer.

Reference Example 18

Preparation of Canine Interferon-γ Having Defective Sugar Chain Using *Bombyx mori* Larvae A virus solution of the gene recombinant baculoviruses rBNVγS2(−) shown in Reference Example 3 was inoculated into *Bombyx mori* larvae in the fifth stage and second day, and fed on commercial artificial feed (produced by Kanebo Silk Elegance Co., Ltd.) at 25° C. for 4 days. The abdomens of 50 larvae were incised, immersed in 500 ml of 50 mM acetic acid buffer (pH 3.5) containing 0.01% benzalkonium chloride, and then maintained at 4° C. for 20 hours. The resultant *Bombyx mori* hemolymph extract was neutralized with 2N NaCl, and then centrifuged at 5000 rpm for 15 minutes to recover a supernatant. The thus-obtained supernatant was subjected to ultrafiltration using a holofiber type ultrafilter (produced by Amicon Co., Ltd., the molecular weight fraction size 100,000, HIP40-100). The resultant filtrate was poured into a column filled with a sulfopropyl cellulose carrier (high performance type, produced by Pharmacia Co., Ltd.), and washed with a 20 mM phosphoric acid buffer (pH 7.0). The adsorbate was then eluted with sodium chloride at a linear concentration gradient, and a fraction having antiviral activity was collected to recover canine IFN-γ. The thus-obtained fraction was poured into a column filled with Blue sepharose carrier (produced by Pharmacia Biotech Co., Ltd.), and washed with a 20 mM phosphoric acid buffer (pH 7.0). The adsorbate was then eluted with 1 to 1.5 M sodium chloride, and a fraction having antiviral activity was collected to recover canine IFN-γ. The thus-obtained canine IFN-γ was dialyzed overnight in a 20 mM sodium phosphate buffer (pH 7.0), and then used as a canine IFN-γ sample for examining a stabilizer.

Reference Example 19

Preparation of Canine Interferon-γ Using *Escherichia coli*

*Escherichia coli* (BL21 strain), into which a vector (pET) into which a gene coding for canine IFN-γ was integrated was introduced, was inoculated into a LB liquid medium, and IPTG was added to the medium in the logarithmic growth phase so that the final concentration was 1 mM. 2 hours after, cells were collected, suspended in a 20 mM sodium phosphate buffer (pH 7.0) in a volume of 1/50 of that at the time of culture, crushed by ultrasonic waves, and then centrifuged at 14000 rpm. The thus-obtained supernatant was filtered with a sterilizing filter of 4.5 μm to obtain a IFN-γ extract.

The extract was purified by a sulfopropyl sepharose column (high performance type, produced by Pharmacia Co., Ltd.). Specifically, the extract was applied to the column, washed with a 20 mM sodium phosphate buffer (pH 7.0) and further washed with a 20 mM sodium phosphate buffer (pH 7.0) containing 0.4 M NaCl. The extract was then eluted stepwisely with sodium phosphate buffers containing 0.5M, 0.6M, 0.7M, 0.8M, 0.9M and 1.0M NaCl. The resultant eluted fractions were subjected to SDS-PAGE, and fractions containing IFN-γ were further purified with blue sepharose (fast flow type). Specifically, the fractions containing IFN-γ were collected, applied to the column, washed with a sodium phosphate buffer (pH 7.0) containing 0.5M NaCl, and further washed with a sodium phosphate buffer (pH 7.0) containing 1.0M NaCl, followed by stepwise elution with sodium phosphate buffers containing 1.5M, 2.0M and 2.0M NaCl. to A 2.0M eluted fraction obtained as a canine IFN-γ fraction was then dialyzed overnight in a 20 mM sodium phosphate buffer (pH 7.0). After dialysis, the fraction was used as a canine IFN-γ sample for researching a stabilizer.

Comparative Example 1

Changes in activity of the canine IFN sample (dissolved in a 20 mM sodium phosphate buffer pH 7.0) obtained in Reference Example 17 were examined when the sample was cold-stored with no other additives added, freeze-stored, and freeze-dried with no stabilizer added. The residual rate of activity is shown based on 100% of activity of the sample before treatment. The results are shown in Table 9.

The freeze-dried sample was dissolved again in sterilized distilled water, and supplied to measurement of antiviral activity.

TABLE 9

Storage method and activity of canine IFN-γ with no stabilizer added

| Storage method | Rate of residual activity (%) |
|---|---|
| Cold-storage for 2.5 days | 71.0 |
| Freeze-storage for 2.5 days | 17.0 |
| Freeze-drying | 35.4 |

Example 1

The canine IFN-γ sample (dissolved in a 20 mM sodium phosphate buffer at pH 7.0) extracted from *Bombyx mori* and purified in Reference Example 17 was mixed with 1 ml each of various concentrations (final concentrations) of aqueous gum arabic solutions (5.0, 7.5, 10.0, 12.5, 15.0, and 20.0 mg/ml) in a glass vial, freeze-dried, and then again dissolved to measure residual activity and the rate of residual activity ($1.24 \times 10^5$ U was considered as 100%). The results are shown in Table 10.

TABLE 10

Amount of gum arabic added and canine IFN-γ activity

| Gum arabic (mg) | Residual activity (U) | Rate of residual activity (%) |
|---|---|---|
| 5.0 | $1.47 \times 10^5$ | 119 |
| 7.5 | $1.10 \times 10^5$ | 88 |
| 10.0 | $1.97 \times 10^5$ | 158 |
| 12.5 | $1.39 \times 10^5$ | 112 |
| 15.0 | $1.19 \times 10^5$ | 96 |
| 20.0 | $1.55 \times 10^5$ | 125 |

Example 2

1 ml of aqueous solution containing the canine IFN-γ sample (dissolved in a 20 mM sodium phosphate buffer at pH 7.0) extracted from *Bombyx mori* and purified in Reference Example 17 and each of aqueous gum arabic solutions (final concentration of 10.0 mg/ml) showing various pH values was freeze-dried in a glass vial and then again dissolved to measure residual activity and the rate of residual activity ($1.24 \times 10^5$ U was considered as 100%). The results are shown in Table 11. The pH values of the aqueous gum arabic solutions were measured after an appropriate amount of HCl as an acid or NaOH as an alkali was added thereto, and the measurements are shown in the table. The moisture content of the freeze-dried sample was about 1.8% (the average of three measurements), and the content of gum arabic (% by weight) in the freeze-dried sample was about 98.2%.

TABLE 11 pH and canine IFN-γ activity with the gum arabic added

| pH (measurement) | Residual activity (U) | Rate of residual activity (%) |
|---|---|---|
| 4.23 | $1.21 \times 10^5$ | 98 |
| 4.54 | $1.60 \times 10^5$ | 129 |
| 4.94 | $1.94 \times 10^5$ | 156 |
| 5.22 | $1.38 \times 10^5$ | 111 |
| 5.45 | $2.13 \times 10^5$ | 172 |
| 6.81 | $2.00 \times 10^5$ | 161 |
| 9.01 | $1.27 \times 10^5$ | 102 |

Example 3

The canine IFN-γ sample (dissolved in a 20 mM sodium phosphate buffer at pH 7.0) extracted from recombinant *Escherichia coli* and purified in Reference Example 19 was mixed with each of aqueous gum arabic solutions adjusted to various pH values with HCl and NaOH, and 1 ml (the final concentration of gum arabic of 10 mg/ml) of each of the resultant mixtures was stored at 4° C. for 6 days. The residual activities and the rates of residual activities ($1.20 \times 10^5$ was considered as 100%) measured after storage are shown in Table 12.

TABLE 12

Influence of pH on canine IFN-γ activity in aqueous gum arabic solution

| pH | Residual activity (U) | Rate of residual activity (%) |
|---|---|---|
| 3.0 | $2.3 \times 10^3$ | 19.2 |
| 3.5 | $1.2 \times 10^3$ | 14.2 |
| 4.0 | $2.0 \times 10^3$ | 16.0 |
| 4.5 | $8.4 \times 10^4$ | 70.0 |
| 5.0 | $8.5 \times 10^4$ | 70.8 |
| 5.5 | $8.5 \times 10^4$ | 70.8 |
| 6.0 | $2.1 \times 10^5$ | 175.0 |
| 7.0 | $9.9 \times 10^4$ | 83.1 |
| 7.5 | $1.8 \times 10^5$ | 150.0 |
| 8.0 | $1.7 \times 10^5$ | 141.0 |

Example 4

1 mL of mixture solution containing the canine IFN-γ sample (dissolved in a 20 mM sodium phosphate buffer at pH 7.0) extracted from recombinant *Escherichia coli* and purified in Reference Example 19 and each of aqueous gum arabic solutions (final concentration of 10.0 mg/ml) adjusted to various pH values was placed in a glass vial and freeze-dried. The thus freeze-dried product was dissolved again to measure residual activity and the rate of residual activity ($4.0 \times 10^5$ U was considered as 100%). The results are shown in Table 13. The moisture content of the freeze-dried sample was about 1.7% (the average of three measurements), and the content of gum arabic (% by weight) in the freeze-dried sample was about 98.3%.

TABLE 13 pH and canine IFN-γ activity with the gum arabic added

| pH (measurement) | Residual activity (U) | Rate of residual activity (%) |
|---|---|---|
| 4.02 | $1.4 \times 10^4$ | 3.5 |
| 4.36 | $2.5 \times 10^5$ | 62.5 |
| 4.61 | $4.4 \times 10^5$ | 111.0 |

TABLE 13-continued pH and canine IFN-γ activity with the gum arabic added

| pH (measurement) | Residual activity (U) | Rate of residual activity (%) |
|---|---|---|
| 4.86 | $5.6 \times 10^5$ | 140.0 |
| 4.90 | $3.9 \times 10^5$ | 97.5 |
| 5.03 | $6.2 \times 10^5$ | 155.0 |
| 5.24 | $4.8 \times 10^5$ | 120.0 |
| 8.20 | $3.5 \times 10^5$ | 87.5 |

Example 5

The canine IFN-γ sample (dissolved in a 20 mM sodium phosphate buffer at pH 7.0) extracted from *Bombyx mori* and purified in Reference Example 17 was mixed with an aqueous solution containing gum arabic and Rheodol (Tween 20) to prepare a canine IFN-γ solution containing 10 mg/ml of gum arabic and 0 to 0.1% of Rheodol. 1 mL of the thus-prepared canine IFN-γ solution was placed in a glass vial, freeze-dried, and then dissolved again to examine the residual activity and the rate of residual activity ($1.24 \times 10^5$ U was considered as 100%). The moisture content of the freeze-dried sample was about 1.7% (the average of three measurements). Table 14 shows the residual activity and the content of gum arabic (% by weight) of each of freeze-dried samples.

TABLE 14 concentration and canine IFN-γ activity in the presence of gum arabic

| Gum arabic (mg/ml) | Rheodol (% by weight) | Residual activity (U) | Residual rate (%) | Content of gum arabic after freeze-drying (% by weight) |
|---|---|---|---|---|
| 10.0 | 0 | $1.97 \times 10^5$ | 158 | 98.1 |
| 10.0 | 0.01 | $1.78 \times 10^5$ | 143 | 98.1 |
| 10.0 | 0.02 | $1.64 \times 10^5$ | 137 | 98.1 |
| 10.0 | 0.05 | $1.51 \times 10^5$ | 122 | 98.0 |
| 10.0 | 0.10 | $1.90 \times 10^5$ | 153 | 98.0 |
| 10.0 | 0.20 | $1.85 \times 10^5$ | 149 | 97.9 |

Example 6

The canine IFN-γ sample (dissolved in a 20 mM sodium phosphate buffer at pH 7.0) extracted from *Bombyx mori* and purified in Reference Example 17 was mixed with an aqueous solution containing gum arabic and macrogol 4000 (polyethylene glycol 4000) to prepare a canine IFN-γ solution containing 10 mg/ml of gum arabic and 0 to 10.0 mg/ml of macrogol. 1 mL of the thus-prepared canine IFN-γ solution was placed in a glass vial, freeze-dried, and then dissolved again to examine the residual activity and the rate of residual activity ($1.24 \times 10^5$ U was considered as 100%). The moisture content of the freeze-dried samples was about 1.7% (the average of three measurements). Table 15 shows the residual activity and the content of gum arabic (% by weight) of each of freeze-dried samples.

TABLE 15

Macrogol concentration and canine IFN-γ activity in the presence of gum arabic

| Gum arabic (mg/ml) | Macrogol (mg/ml) | Residual activity (U) | Residual rate (%) | Content of gum arabic after freeze-drying (% by weight) |
|---|---|---|---|---|
| 10.0 | 0 | $1.67 \times 10^5$ | 135 | 98.3 |
| 10.0 | 2.5 | $1.37 \times 10^5$ | 110 | 78.3 |
| 10.0 | 5.0 | $1.46 \times 10^5$ | 118 | 65.0 |
| 10.0 | 10.0 | $1.52 \times 10^5$ | 123 | 48.3 |

Example 7

The canine IFN-γ sample (dissolved in a 20 mM sodium phosphate buffer at pH 7.0) extracted from *Escherichia coli* and purified in Reference Example 19 was mixed with an aqueous solution containing gum arabic and macrogol 4000 (polyethylene glycol 4000) to prepare a canine IFN-γ solution containing 0 to 2.0 mg/ml of gum arabic and 5.0 mg/ml of macrogol. 1 mL of the thus-prepared canine IFN-γ solution was placed in a glass vial, freeze-dried, and then dissolved again to examine the residual activity and the rate of residual activity ($1.0 \times 10^5$ U was considered as 100%).

The moisture content of the freeze-dried samples was about 1.5% (the average of three measurements). Table 16 shows the residual activity and the content of gum arabic (% by weight) of each of freeze-dried samples.

TABLE 16

Amount of gum arabic added and canine IFN-γ activity in the presence of macrogol

| Gum arabic (mg/ml) | Macrogol (mg/ml) | Residual activity (U) | Residual rate (%) | Content of gum arabic after freeze-drying (% by weight) |
|---|---|---|---|---|
| 0 | 5.0 | $3.81 \times 10^4$ | 38 | 98.3 |
| 0.5 | 5.0 | $9.75 \times 10^5$ | 97 | 7.5 |
| 1.0 | 5.0 | $1.12 \times 10^5$ | 112 | 15.2 |
| 2.0 | 5.0 | $1.18 \times 10^5$ | 118 | 27.1 |

Example 8

The canine IFN-γ sample (dissolved in a 20 mM sodium phosphate buffer at pH 7.0) extracted from recombinant *Escherichia coli* and purified in Reference Example 19 was used for preparing canine IFN-γ aqueous solutions adjusted to various pH values and containing 10 mg/ml of gum arabic, 5 mg/ml of macrogol 4000 (polyethylene glycol) and 20 mM glycine. The thus-prepared aqueous solutions were freeze-dried, and then dissolved again to examine the residual activity. Table 17 shows the rates of residual activity when the initial canine IFN-γ activity was considered as 100%. The same test was repeated twice, and the results of Test Nos. 1 and 2 are shown in the table. The moisture content of the freeze-dried samples was about 1.7% (the average of three measurements), and the content of gum arabic (% by weight) of each of freeze-dried samples was about 58.8%.

TABLE 17 pH and residual activity of canine IFN-γ after freeze-drying

| pH | Residual activity (%) | |
|---|---|---|
|  | Test No. 1 | Test No. 2 |
| 4.5 | 110 | 156 |
| 5.0 | 81 | 159 |
| 5.5 | 164 | 148 |
| 6.0 | 100 | 203 |
| 6.5 | 80 | 156 |
| 7.0 | 136 | 178 |

Example 9

The canine IFN-γ sample (dissolved in a 20 mM sodium phosphate buffer at pH 7.0) extracted from *Bombyx mori* and purified in Reference Example 17 was mixed with 10 mg/ml of gum arabic, 5 mg/ml of macrogol 4000 (polyethylene glycol 4000) and 10 mM of glycine. A total of 1 ml of the thus-prepare solution was placed in a glass vial, freeze-dried, and then dissolved again to examine residual activity. As a result, in dissolution after freeze-drying, the activity was $5.4 \times 10^4$ U, and 90% of the initial canine IFN-γ activity of $6.0 \times 10^4$ U remained.

INDUSTRIAL APPLICABILITY

Mixing with a compound having the basic skeleton of arabic acid enables stable storage of a useful-protein such as interferon or the like without inactivation thereof, thereby permitting applications in various industrial fields such as the medical field.

REFERENCES

1. Devos et al.: J. Interferon Research, 12, 95–102 (1992)
2. Ijzerman et al.: Immunobiology, 179, 456–473 (1989)
3. Chirgwin et al.: Biochemistry, 18, 5294 (1979)
4. Berger et al.: Biochemistry, 18, 5143 (1979)
5. Gubler et al.: Gene, 25, 236–269 (1983)
6. Okayama et al.: Mol. Cell. Biol., 2, 161, (1982) & 3, 280, (1983)
7. T. Horiuchi et al.: Agric. Biol. Chem., 51, 1573–1580 (1987)
8. Gardiner et al.: J. Invertebrate Phathol. 25, 363–370 (1975)
9. S. Watanabe et al.: Japan I. Exp. Med., 21, 299–313 (1951)
10. N. Yamamoto et al.: Bokin Bobai, 16, 505–508 (1988)
11. M. Watanabe et al.: Nihon Kiitogaku Zasshi, 37, 213–218 (1968)
12. Molecular Cloning, Cold Spring Harbor Laboratory, New York, 1982
13. Takebe et al.: Mol. Cell. Biol., 8, 446–472 (1988)
14. Biochemical Society of Japan: Zoku Seikagaku Jikkenkoza, Vol. 5 (1986), P250–256, Tokyo Kagaku Dojin
15. Yamamoto et al.: Vet. Immunol. and Immunopathol., 11, 1–19 (1986)
16. Whiterside et al.: J. Immunol. Methods, 90, 221–223 (1986)
17. Modern Biology Series 23, Animal Tissue Culture Method (1976), 296–300, Kyoritsu Shuppan (1976)

What is claimed is:

1. A method of stabilizing a useful protein comprising mixing a useful protein and an aqueous solution of a compound having the basic structure of arabic acid to stabilize said useful protein, thereby maintaining biological activity of said useful protein wherein said useful protein is any protein having biological activity in the presence of said compound having the basic structure of arabic acid and wherein said compound having the basic structure of arabic acid is capable of stably maintaining the biological activity of said useful protein.

2. The method of stabilizing a useful protein according to claim 1, comprising mixing said useful protein with 0.01 to 10.0% by weight of a compound having the basic structure of arabic acid.

3. The method of stabilizing a useful protein according to claim 1 or 2, further comprising freeze-drying the useful protein mixed with an aqueous solution of a compound having the basic structure of arabic acid.

4. The method of stabilizing a useful protein according to claim 1, wherein the compound having the basic structure of arabic acid is gum arabic.

5. The method of stabilizing a useful protein according to claim 1, wherein the useful protein is a cytokine.

6. The method of stabilizing a useful protein according to claim 5, wherein said cytokine is an interferon selected from interferon-α, interferon-β, interferon-γ and interferon-ω.

7. The method of stabilizing a useful protein according to claim 6, wherein the said interferferon is a vertebrate interferon.

8. The method of stabilizing a useful protein according to claim 7, wherein said vertebrate interferon is canine interferon-γ or feline interferon-ω.

9. The method of stabilizing a useful protein according to claim 8, wherein said canine interferon-γ is produced from recombinant *Escherichia coli* or recombinant *Bombyx mori*.

* * * * *

UNITED STATES PATENT AND TRADEMARK OFFICE
CERTIFICATE OF CORRECTION

PATENT NO.     : 6,391,296 B1
DATED          : May 21, 2002
INVENTOR(S)    : Okano et al.

It is certified that error appears in the above-identified patent and that said Letters Patent is hereby corrected as shown below:

Column 3,
Line 24, please change "synthe sized" to -- synthesized --.

Column 6,
Line 15, please change "vaculovi-" to -- baculovi- --.

Column 7,
Line 46, please change "culture(s)" to -- culture (5) --.

Column 8,
Line 56, please change "pit" to -- pH --.

Column 11,
Line 7, please insert -- a -- before "cruel".

Column 12,
Line 40, please change "CDNA" to -- cDNA --; and
Line 41, please change "microcentriefuge" to -- microcentrifugal --.

Column 15,
Line 23, please change "5'ATCAACACGCACGAATCTAACGCT3' to
-- 5'ATCAACAACGCACAGAATCTAACGCT3' --

Column 18,
Line 53, please change "50 11" to -- 50 $\mu$1 --; and
Line 62, please change "pSRay" to -- pSR$\alpha\gamma$ --.

Column 22,
Line 19, please change "BNV$\gamma$" to -- rBNV$\gamma$ --.

UNITED STATES PATENT AND TRADEMARK OFFICE
CERTIFICATE OF CORRECTION

PATENT NO. : 6,391,296 B1
DATED : May 21, 2002
INVENTOR(S) : Okano et al.

It is certified that error appears in the above-identified patent and that said Letters Patent is hereby corrected as shown below:

<u>Column 25,</u>
Line 54, please delete "gene".

Signed and Sealed this

Fourteenth Day of January, 2003

JAMES E. ROGAN
*Director of the United States Patent and Trademark Office*

SEQUENCE LISTING

<160> NUMBER OF SEQ ID NOS: 35

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 1
gcgaattcat gaattataca agctatatct tagct         35

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 2
gcgaattctt atttcgatgc tctgcggcct cgaaa         35

<210> SEQ ID NO 3
<211> LENGTH: 501
<212> TYPE: DNA
<213> ORGANISM: Canis familiaris

```
<400> SEQUENCE: 3 atg aat tat aca agc tat atc tta gct ttt cag ctt tgc gtg att ttg      48
Met Asn Tyr Thr Ser Tyr Ile Leu Ala Phe Gln Leu Cys Val Ile Leu
            -20                 -15                 -10 tgt tct tct ggc tgt aac tgt cag gcc atg ttt ttt aaa gaa ata gaa      96
Cys Ser Ser Gly Cys Asn Cys Gln Ala Met Phe Phe Lys Glu Ile Glu
        -5                   1               5 aac cta aag gaa tat ttt aat gca agt aat cca gat gta tcg gac ggt     144
Asn Leu Lys Glu Tyr Phe Asn Ala Ser Asn Pro Asp Val Ser Asp Gly
         10                  15                  20 ggg tct ctt ttc gta gat att ttg aag aaa tgg aga gag gag agt gac     192
Gly Ser Leu Phe Val Asp Ile Leu Lys Lys Trp Arg Glu Glu Ser Asp
 25                  30                  35                  40 aaa aca atc att cag agc caa att gtc tct ttc tac ttg aaa ctg ttt     240
Lys Thr Ile Ile Gln Ser Gln Ile Val Ser Phe Tyr Leu Lys Leu Phe
                 45                  50                  55 gac aac ttt aaa gat aac cag atc att caa agg agc atg gat acc atc     288
Asp Asn Phe Lys Asp Asn Gln Ile Ile Gln Arg Ser Met Asp Thr Ile
             60                  65                  70 aag gaa gac atg ctt ggc aag ttc tta aat tca tcc acc agt aag agg     336
Lys Glu Asp Met Leu Gly Lys Phe Leu Asn Ser Ser Thr Ser Lys Arg
         75                  80                  85 gag gac ttc ctt aag ctg att caa att cct gtg aac gat ctg cag gtc     384
Glu Asp Phe Leu Lys Leu Ile Gln Ile Pro Val Asn Asp Leu Gln Val
     90                  95                 100 cag cgc aag gcg ata aat gaa ctc atc aaa gtg atg aat gat ctc tca     432
Gln Arg Lys Ala Ile Asn Glu Leu Ile Lys Val Met Asn Asp Leu Ser
105                 110                 115                 120 cca aga tcc aac cta agg aag cgg aaa agg agt cag aat ctg ttt cga     480
Pro Arg Ser Asn Leu Arg Lys Arg Lys Arg Ser Gln Asn Leu Phe Arg
                125                 130                 135 ggc cgc aga gca tcg aaa taa                                         501
Gly Arg Arg Ala Ser Lys
            140

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 4
atgaattata caagctatat cttagct                                        27

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 5
ttttcactgc attctagttg tggtttgtcc                                     30

<210> SEQ ID NO 6
<211> LENGTH: 42
<212> TYPE: DNA
<213> ORGANISM: Artificial Sequence
<220> FEATURE:
```

<223> OTHER INFORMATION: Description of Artificial Sequence:Synthetic
      Oligonucleotide

<400> SEQUENCE: 6
ccgaccatgg ctcaggccat gttttttaaa gaaatagaaa ac                          42

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 7
ggatccttat ttcgatgctc tgcggcctcg aaacag                                 36

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 8
acgtggaatt catgcaggcc atgttttttta aagaa                                 35

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 9
cgaagcttca agatctttat ttcgatgctc tgcggcctcg aaacag                      46

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 10
atgaattata caagctatat cttagct                                           27

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 11
atcaacaacg cacagaatct aacgct                                            26

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence:Synthetic Oligonucleotide

<210> SEQ ID NO 12

<400> SEQUENCE: 12
gcagatctat caattataca agctatatct tagct                          35

<210> SEQ ID NO 13
<211> LENGTH: 517
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 13
gcagatctat gaattataca agctatatct tagcttttca gctttgcgtg attttgtgtt     60
cttctggctg taactgtcag gccatgtttt ttaaagaaat agaaaccta aggaatatt     120 ttcaggcaag taatccagat gtatcggacg gtgggtctct tttcgtagat attttgaaga   180
aatggagaga ggagagtgac aaaacaatca ttcagagcca aattgtctct ttctacttga   240
aactgtttga caactttaaa gataaccaga tcattcaaag gagcatggat accatcaagg   300
aagacatgct tggcaagttc ttacagtcat ccaccagtaa gagggaggac ttccttaagc   360
tgattcaaat tcctgtgaac gatctgcagg tccagcgcaa ggcgataaat gaactcatca   420
aagtgatgaa tgatctctca ccaagatcca acctaaggaa gcggaaaagg agtcagaatc   480
tgtttcgagg ccgcagagca tcgaaataag aattcgc                            517

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 14
ataggatcca tgaattatac aagctatatc                                    30

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 15
ctggatatct ggattacttg cctgaaaata ttc                                33

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 16
ccatacgtat cggacggtgg gtctctt                                       27

<210> SEQ ID NO 17
<211> LENGTH: 36
<212> TYPE: DNA
<213> ORGANISM: Artificial Sequence

```
<220> FEATURE:
<223> OTHER INFORMATION: Description of Artificial Sequence:Synthetic
      Oligonucleotide

<400> SEQUENCE: 17
ggtggtcgac tgtaagaact tgccaagcat gtcttc                               36

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 18
ccgatatcca ccagtaagag ggaggacttc cttaag                               36

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 19
ctcgaattct tatttcgatg ctctgcggcc tcg                                  33

<210> SEQ ID NO 20
<211> LENGTH: 147
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 20
ataggatcca tgaattatac aagctatatc ttagcttttc agctttgcgt gattttgtgt     60
tcttctggct gtaactgtca ggccatgttt tttaaagaaa tagaaaacct aaggaatat     120 tttcaggcaa gtaatccaga tatccag                                       147

<210> SEQ ID NO 21
<211> LENGTH: 201
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 21
ccatacgtat cggacggtgg gtctcttttc gtagatattt tgaagaaatg gagagaggag     60
agtgacaaaa caatcattca gagccaaatt gtctctttct acttgaaact gtttgacaac    120
tttaaagata accagatcat tcaaaggagc atggatacca tcaaggaaga catgcttggc    180
aagttcttac agtcgaccac c                                             201

<210> SEQ ID NO 22
<211> LENGTH: 195
<212> TYPE: DNA
<213> ORGANISM: Artificial Sequence
<220> FEATURE:
<223> OTHER INFORMATION: Description of Artificial Sequence:Synthetic
      Oligonucleotide
```

<400> SEQUENCE: 22

```
ccgatatcca ccagtaagag ggaggacttc cttaagctga ttcaaattcc tgtgaacgat      60
ctgcaggtcc agcgcaaggc gataaatgaa ctcatcaaag tgatgaatga tctctcacca     120
agatccaacc taaggaagcg gaaaaggagt cagaatctgt ttcgaggccg cagagcatcg    180
aaataagaat tcgag                                                      195
```

<210> SEQ ID NO 23
<211> LENGTH: 517
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 23

```
gcagatctat gaattataca agctatatct tagcttttca gctttgcgtg attttgtgtt     60
cttctggctg taactgtcag gccatgtttt ttaaagaaat agaaaccta aaggaatatt    120
ttaatgcaag taatccagat gtatcggacg gtgggtctct tttcgtagat attttgaaga   180
aatggagaga ggagagtgac aaaacaatca ttcagagcca aattgtctct ttctacttga   240
aactgtttga caactttaaa gataaccaga tcattcaaag gagcatggat accatcaagg   300
aagacatgct tggcaagttc ttaaatagca gcaccagtaa gagggaggac ttccttaagc   360
tgattcaaat tcctgtgaac gatctgcagg tccagcgcaa ggcgataaat gaactcatca   420
aagtgatgaa tgatctctca ccaagatcca acctaaggaa gcggaaaagg agtcagaatc   480
tgtttcgagg ccgcagagca tcgaaataag aattcgc                             517
```

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 24

```
gcggaattct tatcttggtg agagatcatt catcactttg at                        42
```

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 25

```
gcgggatcct tatcttggtg agagatcatt catcactttg at                        42
```

<210> SEQ ID NO 26
<211> LENGTH: 457
<212> TYPE: DNA
<213> ORGANISM: Artificial Sequence
<220> FEATURE:
<223> OTHER INFORMATION: Description of Artificial Sequence:Synthetic Oligonucleotide

<400> SEQUENCE: 26

```
gcagatctat gaattataca agctatatct tagcttttca gctttgcgtg attttgtgtt     60
cttctggctg taactgtcag gccatgtttt ttaaagaaat agaaaccta aaggaatatt    120
```

```
ttcaggcaag taatccagat gtatcggacg gtgggtctct tttcgtagat attttgaaga      180
aatggagaga ggagagtgac aaaacaatca ttcagagcca aattgtctct ttctacttga      240
aactgtttga caactttaaa gataaccaga tcattcaaag gagcatggat accatcaagg      300
aagacatgct tggcaagttc ttacagtcat ccaccagtaa gagggaggac ttccttaagc      360
tgattcaaat tcctgtgaac gatctgcagg tccagcgcaa ggcgataaat gaactcatca      420
aagtgatgaa tgatctctca ccaagataag aattcgc                              457
```

<210> SEQ ID NO 27
<211> LENGTH: 501
<212> TYPE: DNA
<213> ORGANISM: Canis familiaris

<400> SEQUENCE: 27

```
atg aat tat aca agc tat atc tta gct ttt cag ctt tgc gtg att ttg       48
Met Asn Tyr Thr Ser Tyr Ile Leu Ala Phe Gln Leu Cys Val Ile Leu
            -20                 -15                 -10 tgt tct tct ggc tgt aac tgt cag gcc atg ttt ttt aaa gaa ata gaa       96
Cys Ser Ser Gly Cys Asn Cys Gln Ala Met Phe Phe Lys Glu Ile Glu
        -5                   1               5 aac cta aag gaa tat ttt cag gca agt aat cca gat gta tcg gac ggt      144
Asn Leu Lys Glu Tyr Phe Gln Ala Ser Asn Pro Asp Val Ser Asp Gly
     10                  15                  20 ggg tct ctt ttc gta gat att ttg aag aaa tgg aga gag agt gac         192
Gly Ser Leu Phe Val Asp Ile Leu Lys Lys Trp Arg Glu Glu Ser Asp
 25                  30                  35                  40 aaa aca atc att cag agc caa att gtc tct ttc tac ttg aaa ctg ttt      240
Lys Thr Ile Ile Gln Ser Gln Ile Val Ser Phe Tyr Leu Lys Leu Phe
                 45                  50                  55 gac aac ttt aaa gat aac cag atc att caa agg agc atg gat acc atc      288
Asp Asn Phe Lys Asp Asn Gln Ile Ile Gln Arg Ser Met Asp Thr Ile
             60                  65                  70 aag gaa gac atg ctt ggc aag ttc tta cag tca tcc acc agt aag agg      336
Lys Glu Asp Met Leu Gly Lys Phe Leu Gln Ser Ser Thr Ser Lys Arg
         75                  80                  85 gag gac ttc ctt aag ctg att caa att cct gtg aac gat ctg cag gtc      384
Gly Asp Phe Leu Lys Leu Ile Gln Ile Pro Val Asn Asp Leu Gln Val
 90                  95                 100 cag cgc aag gcg ata aat gaa ctc atc aaa gtg atg aat gat ctc tca      432
Gln Arg Lys Ala Ile Asn Glu Leu Ile Lys Val Met Asn Asp Leu Ser
105                 110                 115                 120 cca aga tcc aac cta agg aag cgg aaa agg agt cag aat ctg ttt cga      480
Pro Arg Ser Asn Leu Arg Lys Arg Lys Arg Ser Gln Asn Leu Phe Arg
                125                 130                 135 ggc cgc aga gca tcg aaa taa                                          501
Gly Arg Arg Ala Ser Lys
                140
```

<210> SEQ ID NO 28
<211> LENGTH: 441
<212> TYPE: DNA
<213> ORGANISM: Canis familiaris

<400> SEQUENCE: 28

```
atg aat tat aca agc tat atc tta gct ttt cag ctt tgc gtg att ttg       48
Met Asn Tyr Thr Ser Tyr Ile Leu Ala Phe Gln Leu Cys Val Ile Leu
            -20                 -15                 -10 tgt tct tct ggc tgt aac tgt cag gcc atg ttt ttt aaa gaa ata gaa       96
Cys Ser Ser Gly Cys Asn Cys Gln Ala Met Phe Phe Lys Glu Ile Glu
```

-continued

```
              -5                    1                   5
aac cta aag gaa tat ttt cag gca agt aat cca gat gta tcg gac ggt        144
Asn Leu Lys Glu Tyr Phe Gln Ala Ser Asn Pro Asp Val Ser Asp Gly
         10                  15                  20 ggg tct ctt ttc gta gat att ttg aag aaa tgg aga gag gag agt gac        192
Gly Ser Leu Phe Val Asp Ile Leu Lys Lys Trp Arg Glu Glu Ser Asp
 25                  30                  35                  40 aaa aca atc att cag agc caa att gtc tct ttc tac ttg aaa ctg ttt        240
Lys Thr Ile Ile Gln Ser Gln Ile Val Ser Phe Tyr Leu Lys Leu Phe
                     45                  50                  55 gac aac ttt aaa gat aac cag atc att caa agg agc atg gat acc atc        288
Asp Asn Phe Lys Asp Asn Gln Ile Ile Gln Arg Ser Met Asp Thr Ile
                 60                  65                  70 aag gaa gac atg ctt ggc aag ttc tta cag tca tcc acc agt aag agg        336
Lys Glu Asp Met Leu Gly Lys Phe Leu Gln Ser Ser Thr Ser Lys Arg
             75                  80                  85 gag gac ttc ctt aag ctg att caa att cct gtg aac gat ctg cag gtc        384
Glu Asp Phe Leu Lys Leu Ile Gln Ile Pro Val Asn Asp Leu Gln Val
         90                  95                 100 cag cgc aag gcg ata aat gaa ctc atc aaa gtg atg aat gat ctc tca        432
Gln Arg Lys Ala Ile Asn Glu Leu Ile Lys Val Met Asn Asp Leu Ser
105                 110                 115                 120 cca aga taa                                                            441
Pro Arg <210> SEQ ID NO 29
<211> LENGTH: 453
<212> TYPE: DNA
<213> ORGANISM: Canis familiaris

<400> SEQUENCE: 29 atg aat tat aca agc tat atc tta gct ttt cag ctt tgc gtg att ttg         48
Met Asn Tyr Thr Ser Tyr Ile Leu Ala Phe Gln Leu Cys Val Ile Leu
                 -20                 -15                 -10 tgt tct tct ggc tgt aac tgt cag gcc atg ttt ttt aaa gaa ata gaa         96
Cys Ser Ser Gly Cys Asn Cys Gln Ala Met Phe Phe Lys Glu Ile Glu
             -5                   1                   5 aac cta aag gaa tat ttt cag gca agt aat cca gat gta tcg gac ggt        144
Asn Leu Lys Glu Tyr Phe Gln Ala Ser Asn Pro Asp Val Ser Asp Gly
         10                  15                  20 ggg tct ctt ttc gta gat att ttg aag aaa tgg aga gag gag agt gac        192
Gly Ser Leu Phe Val Asp Ile Leu Lys Lys Trp Arg Glu Glu Ser Asp
 25                  30                  35                  40 aaa aca atc att cag agc caa att gtc tct ttc tac ttg aaa ctg ttt        240
Lys Thr Ile Ile Gln Ser Gln Ile Val Ser Phe Tyr Leu Lys Leu Phe
                     45                  50                  55 gac aac ttt aaa gat aac cag atc att caa agg agc atg gat acc atc        288
Asp Asn Phe Lys Asp Asn Gln Ile Ile Glu Arg Ser Met Asp Thr Ile
                 60                  65                  70 aag gaa gac atg ctt ggc aag ttc tta cag tca tcc acc agt aag agg        336
Lys Glu Asp Met Leu Gly Lys Phe Leu Gln Ser Ser Thr Ser Lys Arg
             75                  80                  85 gag gac ttc ctt aag ctg att caa att cct gtg aac gat ctg cag gtc        384
Glu Asp Phe Leu Lys Leu Ile Gln Ile Pro Val Asn Asp Leu Gln Val
         90                  95                 100 cag cgc aag gcg ata aat gaa ctc atc aaa gtg atg aat gat ctc tca        432
Gln Arg Lys Ala Ile Asn Glu Leu Ile Lys Val Met Asn Asp Leu Ser
105                 110                 115                 120 cca aga tcc aac cta agg taa                                            453
Pro Arg Ser Asn Leu Arg
```

-continued

125

<210> SEQ ID NO 30
<211> LENGTH: 435
<212> TYPE: DNA
<213> ORGANISM: Canis familiaris

<400> SEQUENCE: 30

| atg | cag | gcc | atg | ttt | ttt | aaa | gaa | ata | gaa | aac | cta | aag | gaa | tat | ttt | 48 |
| Met | Gln | Ala | Met | Phe | Phe | Lys | Glu | Ile | Glu | Asn | Leu | Lys | Glu | Tyr | Phe | |
| 1 | | | | 5 | | | | | 10 | | | | | 15 | | |

| aat | gca | agt | aat | cca | gat | gta | tcg | gac | ggt | ggg | tct | ctt | ttc | gta | gat | 96 |
| Asn | Ala | Ser | Asn | Pro | Asp | Val | Ser | Asp | Gly | Gly | Ser | Leu | Phe | Val | Asp | |
| | | | 20 | | | | | 25 | | | | | 30 | | | |

| aat | ttg | aag | aaa | tgg | aga | gag | gag | agt | gac | aaa | aca | atc | att | cag | agc | 144 |
| Ile | Leu | Lys | Lys | Trp | Arg | Glu | Glu | Ser | Asp | Lys | Thr | Ile | Ile | Gln | Ser | |
| | 35 | | | | | 40 | | | | | 45 | | | | | |

| caa | att | gtc | tct | ttc | tac | ttg | aaa | ctg | ttt | gac | aac | ttt | aaa | gat | aac | 192 |
| Gln | Ile | Val | Ser | Phe | Tyr | Leu | Lys | Leu | Phe | Asp | Asn | Phe | Lys | Asp | Asn | |
| 50 | | | | | 55 | | | | | 60 | | | | | | |

| cag | atc | att | caa | agg | agc | atg | gat | acc | atc | aag | gaa | gac | atg | ctt | ggc | 240 |
| Gln | Ile | Ile | Gln | Arg | Ser | Met | Asp | Thr | Ile | Lys | Glu | Asp | Met | Leu | Gly | |
| 65 | | | | | 70 | | | | | 75 | | | | | 80 | |

| aag | ttc | tta | aat | agc | agc | acc | agt | aag | agg | gag | gac | ttc | ctt | aag | ctg | 288 |
| Lys | Phe | Leu | Asn | Ser | Ser | Thr | Ser | Lys | Arg | Glu | Asp | Phe | Leu | Lys | Leu | |
| | | | | 85 | | | | | 90 | | | | | 95 | | |

| att | caa | att | cct | gtc | aac | gat | ctg | cag | gtc | cag | cgc | aag | gcg | ata | aat | 336 |
| Ile | Gln | Ile | Pro | Val | Asn | Asp | Leu | Gln | Val | Gln | Arg | Lys | Ala | Ile | Asn | |
| | | | 100 | | | | | 105 | | | | | 110 | | | |

| gaa | ctc | atc | aaa | gtg | atg | aat | gat | ctc | tca | cca | aga | tcc | aac | cta | agg | 384 |
| Glu | Leu | Ile | Lys | Val | Met | Asn | Asp | Leu | Ser | Pro | Arg | Ser | Asn | Leu | Arg | |
| | | 115 | | | | | 120 | | | | | 125 | | | | |

| aag | cgg | aaa | agg | agt | cag | aat | ctg | ttt | cga | ggc | cgc | aga | gca | tcg | aaa | 432 |
| Lys | Arg | Lys | Arg | Ser | Gln | Asn | Leu | Phe | Arg | Gly | Arg | Arg | Ala | Ser | Lys | |
| | 130 | | | | | 135 | | | | | 140 | | | | | |

| taa | | | | | | | | | | | | | | | | 435 |

<210> SEQ ID NO 31
<211> LENGTH: 166
<212> TYPE: PRT
<213> ORGANISM: Canis familiaris

<400> SEQUENCE: 31

| Met | Asn | Tyr | Thr | Ser | Tyr | Ile | Leu | Ala | Phe | Gln | Leu | Cys | Val | Ile | Leu |
| | | | | -20 | | | | | -15 | | | | | -10 | |

| Cys | Ser | Ser | Gly | Cys | Asn | Cys | Gln | Ala | Met | Phe | Phe | Lys | Glu | Ile | Glu |
| | | | | -5 | | | | | 1 | | | | | 5 | |

| Asn | Leu | Lys | Glu | Tyr | Phe | Asn | Ala | Ser | Asn | Pro | Asp | Val | Ser | Asp | Gly |
| | | 10 | | | | | 15 | | | | | 20 | | | |

| Gly | Ser | Leu | Phe | Val | Asp | Ile | Leu | Lys | Lys | Trp | Arg | Glu | Glu | Ser | Asp |
| 25 | | | | | 30 | | | | | 35 | | | | | 40 |

| Lys | Thr | Ile | Ile | Gln | Ser | Gln | Ile | Val | Ser | Phe | Tyr | Leu | Lys | Leu | Phe |
| | | | | 45 | | | | | 50 | | | | | 55 | |

| Asp | Asn | Phe | Lys | Asp | Asn | Gln | Ile | Ile | Gln | Arg | Ser | Met | Asp | Thr | Ile |
| | | | 60 | | | | | 65 | | | | | 70 | | |

| Lys | Glu | Asp | Met | Leu | Gly | Lys | Phe | Leu | Asn | Ser | Ser | Thr | Ser | Lys | Arg |
| | | 75 | | | | | 80 | | | | | 85 | | | |

| Glu | Asp | Phe | Leu | Lys | Leu | Ile | Gln | Ile | Pro | Val | Asn | Asp | Leu | Gln | Val |
| | | 90 | | | | | 95 | | | | | 100 | | | |

```
Gln Arg Lys Ala Ile Asn Glu Leu Ile Lys Val Met Asn Asp Leu Ser
105                 110                 115                 120

Pro Arg Ser Asn Leu Arg Lys Arg Lys Arg Ser Gln Asn Leu Phe Arg
                125                 130                 135

Gly Arg Arg Ala Ser Lys
                140

<210> SEQ ID NO 32
<211> LENGTH: 166
<212> TYPE: PRT
<213> ORGANISM: Canis familiaris

<400> SEQUENCE: 32

Met Asn Tyr Thr Ser Tyr Ile Leu Ala Phe Gln Leu Cys Val Ile Leu
                -20                 -15                 -10

Cys Ser Ser Gly Cys Asn Cys Gln Ala Met Phe Phe Lys Glu Ile Glu
                -5                   1                   5

Asn Leu Lys Glu Tyr Phe Gln Ala Ser Asn Pro Asp Val Ser Asp Gly
         10                 15                  20

Gly Ser Leu Phe Val Asp Ile Leu Lys Lys Trp Arg Glu Glu Ser Asp
 25                  30                 35                   40

Lys Thr Ile Ile Gln Ser Gln Ile Val Ser Phe Tyr Leu Lys Leu Phe
                45                  50                  55

Asp Asn Phe Lys Asp Asn Gln Ile Ile Gln Arg Ser Met Asp Thr Ile
                 60                  65                  70

Lys Glu Asp Met Leu Gly Lys Phe Leu Gln Ser Ser Thr Ser Lys Arg
         75                  80                  85

Gly Asp Phe Leu Lys Leu Ile Gln Ile Pro Val Asn Asp Leu Gln Val
 90                  95                 100

Gln Arg Lys Ala Ile Asn Glu Leu Ile Lys Val Met Asn Asp Leu Ser
105                 110                 115                 120

Pro Arg Ser Asn Leu Arg Lys Arg Lys Arg Ser Gln Asn Leu Phe Arg
                125                 130                 135

Gly Arg Arg Ala Ser Lys
                140

<210> SEQ ID NO 33
<211> LENGTH: 146
<212> TYPE: PRT
<213> ORGANISM: Canis familiaris

<400> SEQUENCE: 33

Met Asn Tyr Thr Ser Tyr Ile Leu Ala Phe Gln Leu Cys Val Ile Leu
                -20                 -15                 -10

Cys Ser Ser Gly Cys Asn Cys Gln Ala Met Phe Phe Lys Glu Ile Glu
                -5                   1                   5

Asn Leu Lys Glu Tyr Phe Gln Ala Ser Asn Pro Asp Val Ser Asp Gly
         10                 15                  20

Gly Ser Leu Phe Val Asp Ile Leu Lys Lys Trp Arg Glu Glu Ser Asp
 25                  30                 35                   40

Lys Thr Ile Ile Gln Ser Gln Ile Val Ser Phe Tyr Leu Lys Leu Phe
                45                  50                  55

Asp Asn Phe Lys Asp Asn Gln Ile Ile Gln Arg Ser Met Asp Thr Ile
                 60                  65                  70

Lys Glu Asp Met Leu Gly Lys Phe Leu Gln Ser Ser Thr Ser Lys Arg
         75                  80                  85
```

Glu Asp Phe Leu Lys Leu Ile Gln Ile Pro Val Asn Asp Leu Gln Val
    90                  95                  100

Gln Arg Lys Ala Ile Asn Glu Leu Ile Lys Val Met Asn Asp Leu Ser
105                 110                 115                 120

Pro Arg

<210> SEQ ID NO 34
<211> LENGTH: 150
<212> TYPE: PRT
<213> ORGANISM: Canis familiaris

<400> SEQUENCE: 34

Met Asn Tyr Thr Ser Tyr Ile Leu Ala Phe Gln Leu Cys Val Ile Leu
                -20                 -15                 -10

Cys Ser Ser Gly Cys Asn Cys Gln Ala Met Phe Phe Lys Glu Ile Glu
             -5                   1                   5

Asn Leu Lys Glu Tyr Phe Gln Ala Ser Asn Pro Asp Val Ser Asp Gly
            10                  15                  20

Gly Ser Leu Phe Val Asp Ile Leu Lys Lys Trp Arg Glu Glu Ser Asp
 25                  30                  35                  40

Lys Thr Ile Ile Gln Ser Gln Ile Val Ser Phe Tyr Leu Lys Leu Phe
                 45                  50                  55

Asp Asn Phe Lys Asp Asn Gln Ile Ile Glu Arg Ser Met Asp Thr Ile
             60                  65                  70

Lys Glu Asp Met Leu Gly Lys Phe Leu Gln Ser Ser Thr Ser Lys Arg
             75                  80                  85

Glu Asp Phe Leu Lys Leu Ile Gln Ile Pro Val Asn Asp Leu Gln Val
    90                  95                  100

Gln Arg Lys Ala Ile Asn Glu Leu Ile Lys Val Met Asn Asp Leu Ser
105                 110                 115                 120

Pro Arg Ser Asn Leu Arg
                125

<210> SEQ ID NO 35
<211> LENGTH: 144
<212> TYPE: PRT
<213> ORGANISM: Canis familiaris

<400> SEQUENCE: 35

Met Gln Ala Met Phe Phe Lys Glu Ile Glu Asn Leu Lys Glu Tyr Phe
  1               5                  10                  15

Asn Ala Ser Asn Pro Asp Val Ser Asp Gly Gly Ser Leu Phe Val Asp
                 20                  25                  30

Ile Leu Lys Lys Trp Arg Glu Glu Ser Asp Lys Thr Ile Ile Gln Ser
            35                  40                  45

Gln Ile Val Ser Phe Tyr Leu Lys Leu Phe Asp Asn Phe Lys Asp Asn
 50                  55                  60

Gln Ile Ile Gln Arg Ser Met Asp Thr Ile Lys Glu Asp Met Leu Gly
 65                  70                  75                  80

Lys Phe Leu Asn Ser Ser Thr Ser Lys Arg Glu Asp Phe Leu Lys Leu
             85                  90                  95

-continued

```
Ile Gln Ile Pro Val Asn Asp Leu Gln Val Gln Arg Lys Ala Ile Asn
            100                 105                 110

Glu Leu Ile Lys Val Met Asn Asp Leu Ser Pro Arg Ser Asn Leu Arg
            115                 120                 125

Lys Arg Lys Arg Ser Gln Asn Leu Phe Arg Gly Arg Arg Ala Ser Lys
130                 135                 140
```